(12) United States Patent
Whitson et al.

(10) Patent No.: US 7,611,899 B2
(45) Date of Patent: *Nov. 3, 2009

(54) SENSOR RELEASE FOR A SENSOR DISPENSING INSTRUMENT

(75) Inventors: Robert C. Whitson, Elkhart, IN (US); Russell J. Micinski, South Bend, IN (US)

(73) Assignee: Bayer HealthCare LLC, Tarrytown, NY (US)

(*) Notice: Subject to any disclaimer, the term of this patent is extended or adjusted under 35 U.S.C. 154(b) by 553 days.

This patent is subject to a terminal disclaimer.

(21) Appl. No.: 10/206,345

(22) Filed: Jul. 30, 2002

(65) Prior Publication Data

US 2003/0031591 A1 Feb. 13, 2003

Related U.S. Application Data

(60) Provisional application No. 60/311,758, filed on Aug. 13, 2001.

(51) Int. Cl.
*G01N 33/48* (2006.01)

(52) U.S. Cl. .............................. 436/45; 436/43; 422/58; 422/64

(58) Field of Classification Search .................... 422/58, 422/61, 82.05, 62, 64; 436/43, 45, 46, 164, 436/166, 169
See application file for complete search history.

(56) References Cited

U.S. PATENT DOCUMENTS

| | | | |
|---|---|---|---|
| 5,489,414 A | 2/1996 | Schreiber et al. | 422/64 |
| 5,510,266 A | 4/1996 | Bonner et al. | 436/43 |
| 5,575,403 A | 11/1996 | Charlton et al. | |
| 5,630,986 A | 5/1997 | Charlton et al. | |
| 5,660,791 A * | 8/1997 | Brenneman et al. | 422/58 |
| 2003/0031591 A1 | 2/2003 | Whitson et al. | 422/50 |
| 2003/0031599 A1 | 2/2003 | Brown | 422/100 |
| 2003/0089730 A1 | 5/2003 | May et al. | 221/232 |

FOREIGN PATENT DOCUMENTS

| | | |
|---|---|---|
| EP | 1 118 856 A1 | 7/2001 |
| EP | 1 321 769 A1 | 6/2003 |
| EP | 1 475 630 A1 | 11/2004 |
| WO | WO 94/10558 | 5/1994 |
| WO | WO 02/18940 A2 | 3/2002 |

OTHER PUBLICATIONS

Written Opinion corresponding to International Patent Application Serial No. PCT/2006/015848, European Patent Office, dated Aug. 22, 2006, 7 pages.
International Search Report corresponding to International Patent Application Serial No. PCT/2006/05848, European Patent Office, dated Aug. 22, 2006, 3 pages.

* cited by examiner

*Primary Examiner*—Lyle A Alexander
(74) *Attorney, Agent, or Firm*—Nixon Peabody LLP

(57) ABSTRACT

A sensor dispensing instrument adapted to handle a sensor pack containing a plurality of sensors and to perform a test using one of the sensors. The sensor dispensing instrument includes an outer housing and a mechanical mechanism contained therein for rotating the sensor pack and ejecting one of the sensors from the sensor pack and through a sensor slot on the housing. The sensor dispensing instrument also includes a sensor actuator to engage with a sensor disposed in the sensor slot, and a sensor release that is movable to disengage the sensor actuator from the sensor disposed in the sensor slot and permit the discharge of the sensor.

27 Claims, 9 Drawing Sheets

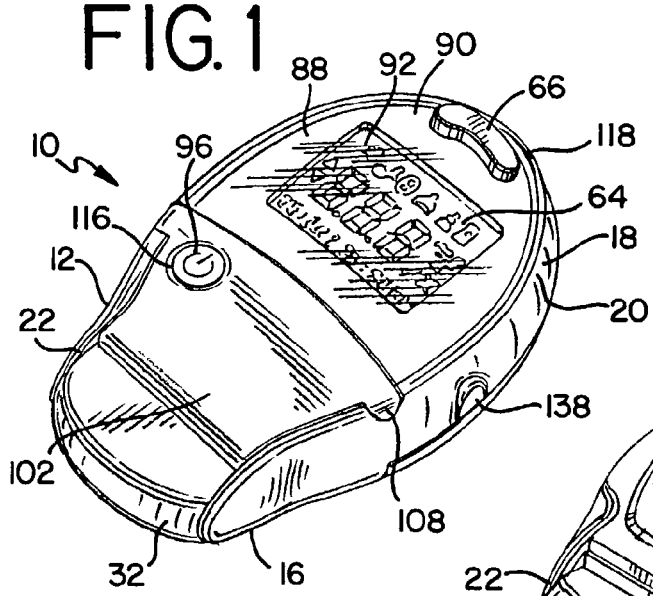
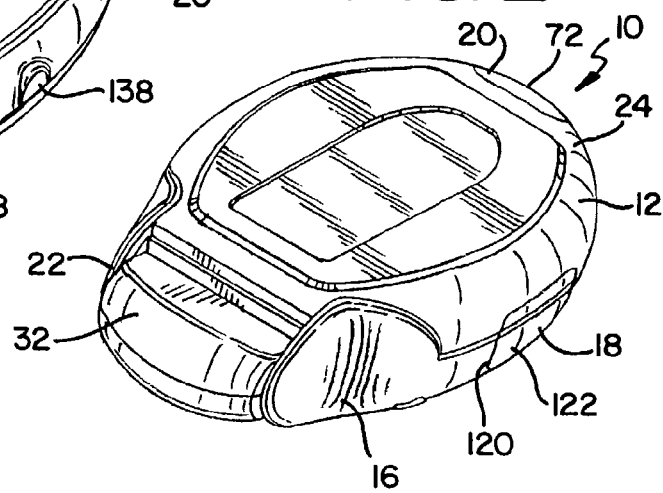
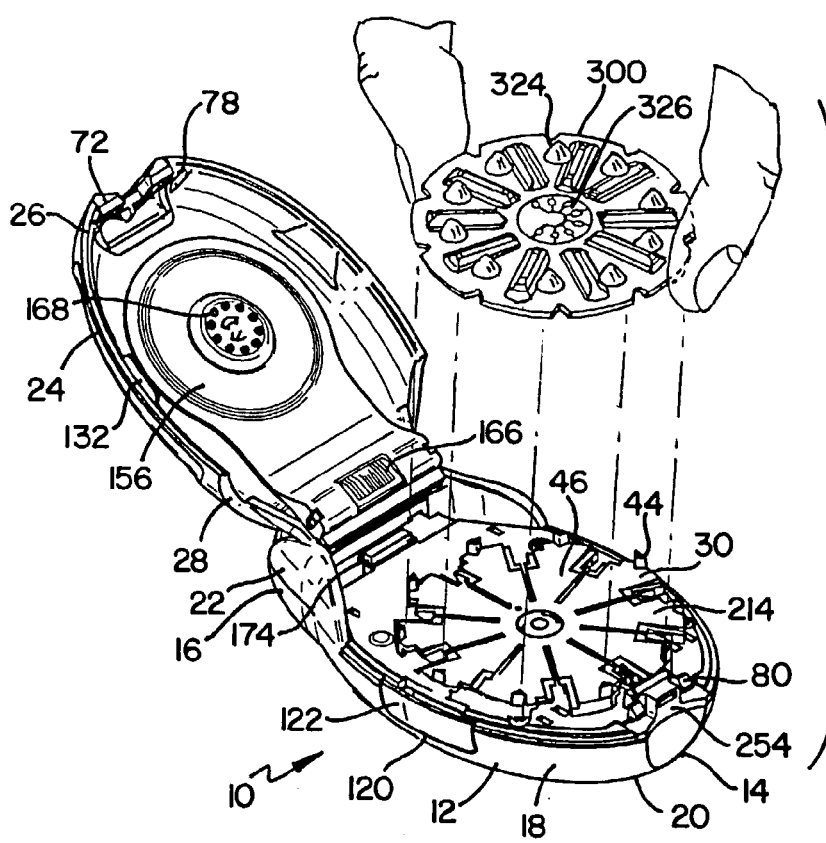

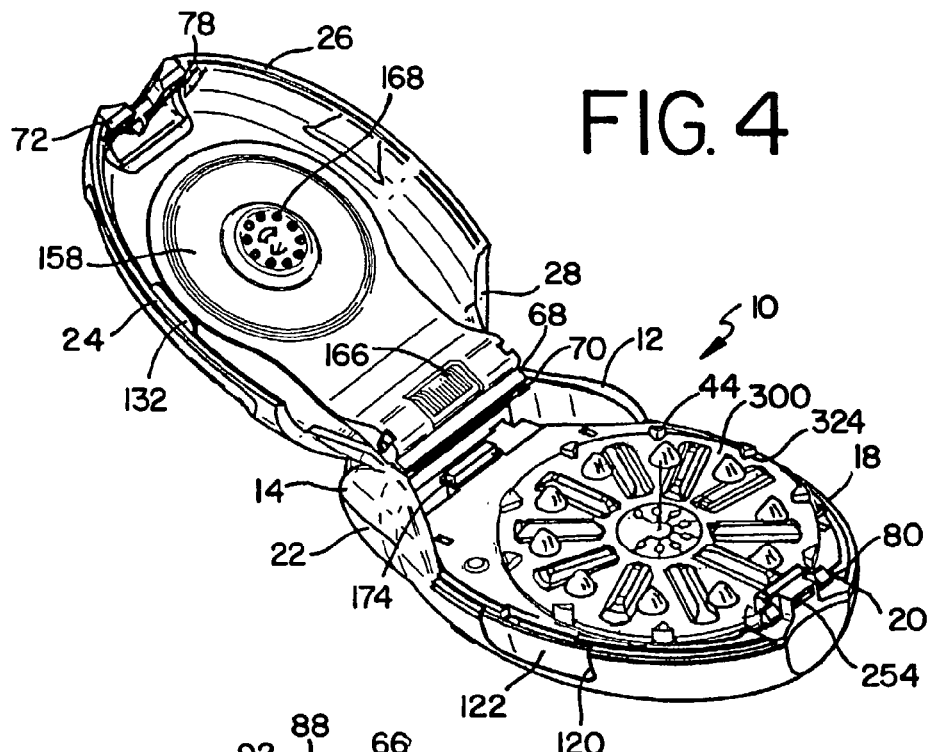
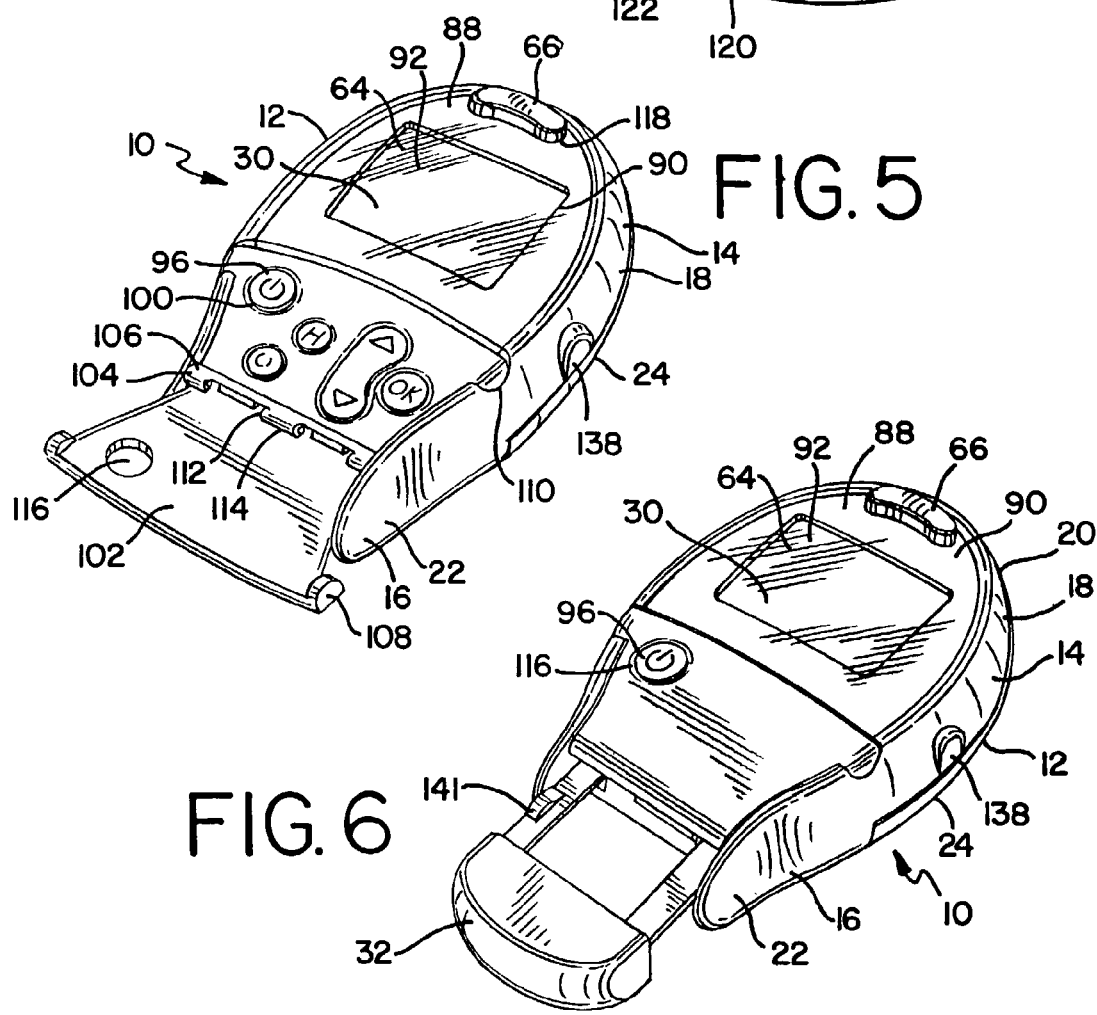

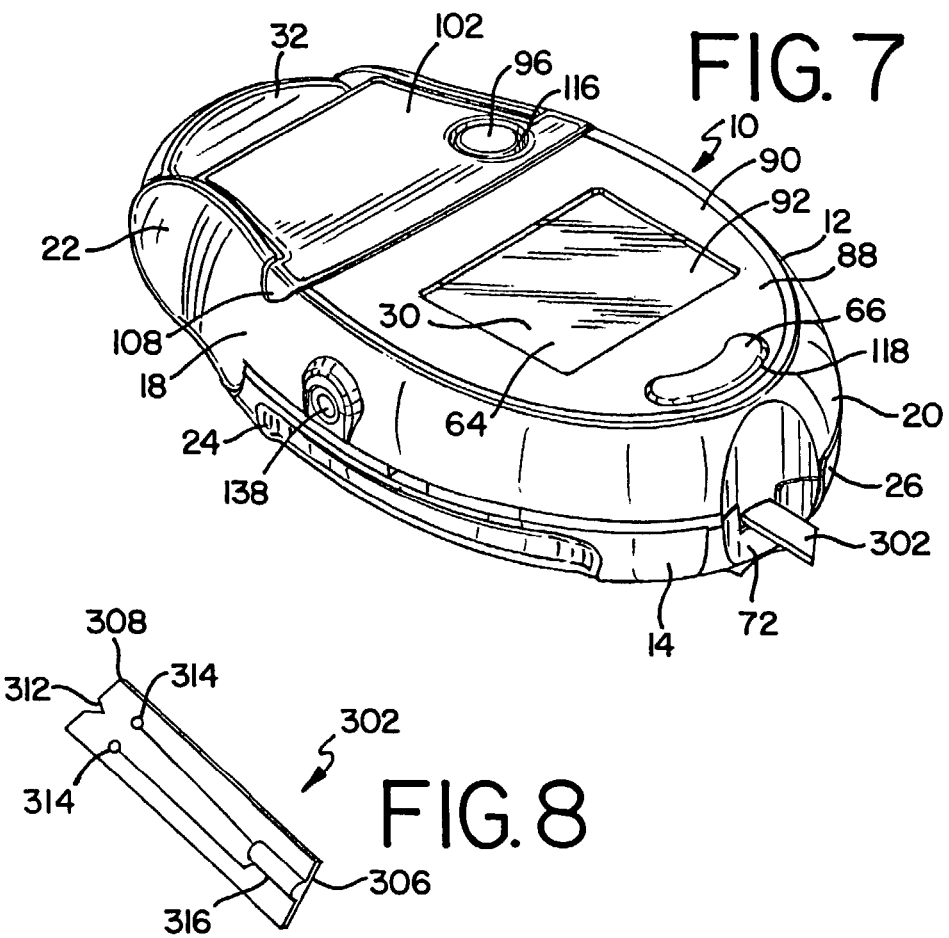
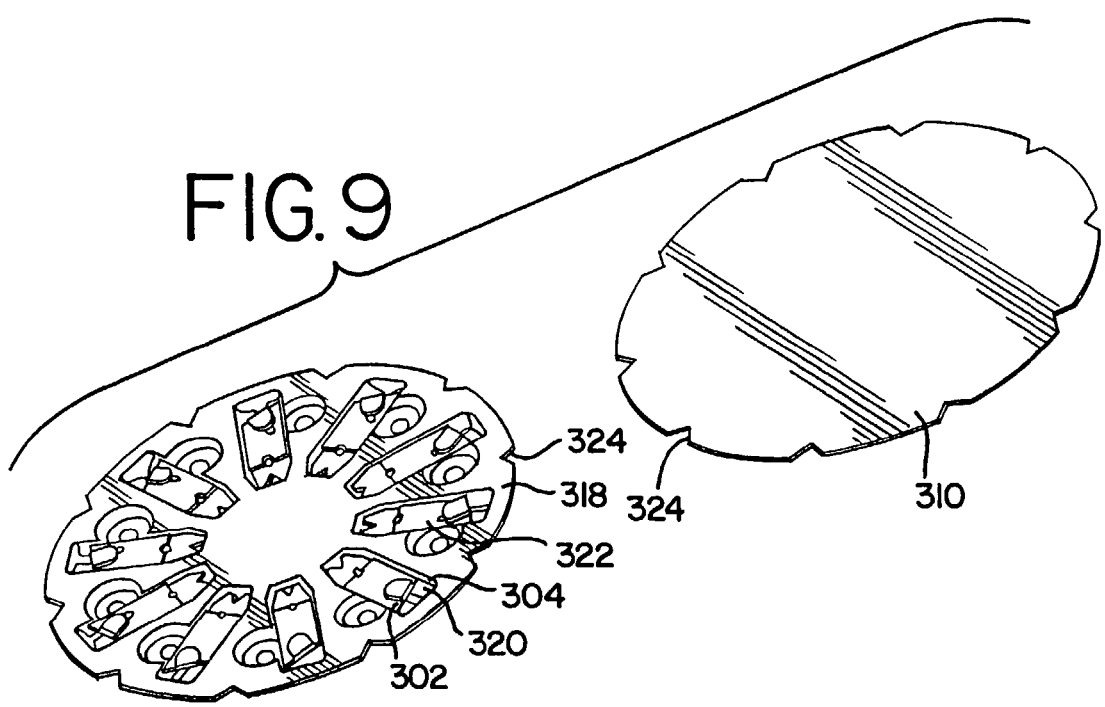

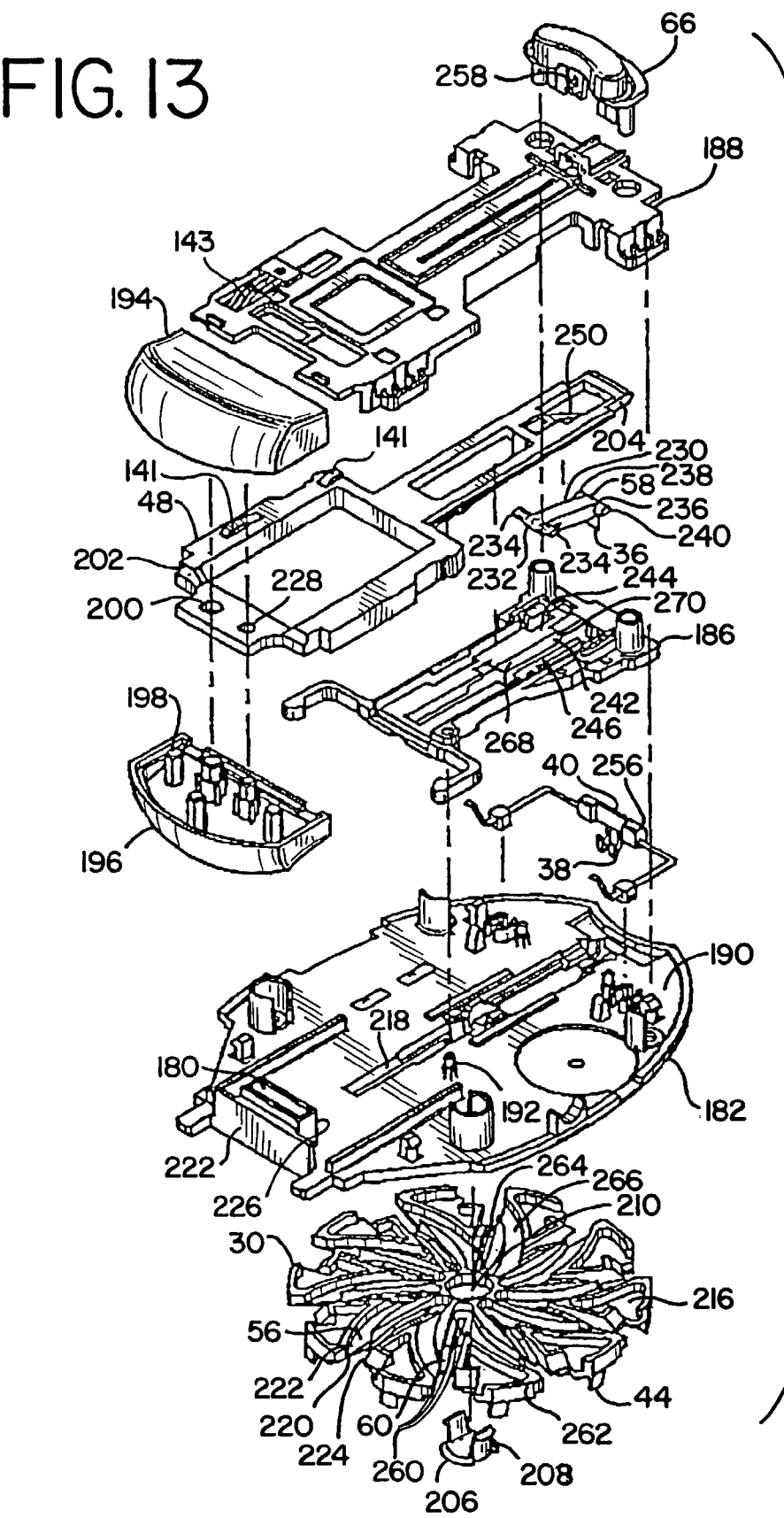

SENSOR RELEASE FOR A SENSOR DISPENSING INSTRUMENT

CROSS REFERENCE TO RELATED APPLICATION

This application claims the benefit of the U.S. Provisional Application 60/311,758, filed on Aug. 13, 2001, which is hereby incorporated by reference in its entirety.

BACKGROUND OF THE INVENTION

1. Field of the Invention

The present invention generally relates to a fluid monitoring system, and, more particularly, to a new and improved instrument for handling multiple sensors that are used in analyzing blood glucose or other analytes contained therein.

2. Description of the Prior Art

People suffering from various forms of diabetes routinely need to test their blood to determine the level of blood glucose. The results of such tests can be used to determine what, if any, insulin or other medication needs to be administered. In one type of blood glucose testing system, sensors are used to test a sample of blood.

Such a sensor may have a generally flat, rectangular shape with a front or testing end and a rear or contact end. The sensor contains biosensing or reagent material that will react with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor with the result that an electrical signal indicative of the blood glucose level in the blood being tested is supplied to contact areas located near the rear or contact end of the sensor.

In order to couple the electrical signals produced at the sensor contacts to monitoring equipment, the sensors need to be inserted into sensor holders prior to the sensor end being placed into the fluid being tested. The holders have corresponding mating contact areas that become coupled to the contacts on the sensor when the sensor is inserted into the holder. Consequently, the holders act as an interface between the sensor and monitoring equipment that accumulates and/or analyzes the test results.

Prior to being used, the sensors need to be maintained at an appropriate humidity level so as to insure the integrity of the reagent materials in the sensor. Sensors can be packaged individually in tear-away packages so that they can be maintained at the proper humidity level. For instance, blister type packaging methods could be used. In this connection, the packages can include desiccant material to maintain the proper humidity in the package. In order for a person to use an individual sensor for testing blood glucose, the package must be opened by tearing the seal. Alternatively, some packages require the user to exert force against one side of the package resulting in the sensor bursting or rupturing the foil on the other side. As can be appreciated, the opening of these packages can be difficult. Moreover, once the package is opened, the user needs to be sure that the sensor is not damaged or contaminated as it is being placed into the sensor holder and used to test the blood sample.

U.S. Pat. No. 5,630,986, issued on May 20, 1997, and entitled Dispensing Instrument For Fluid Monitoring Sensors (referred to hereinafter as "the '986 patent"), discloses a type of sensor pack with multiple sensors and a testing blood glucose and dispensing instrument for handling the sensors contained in such a sensor pack. In particular, the sensor dispensing instrument disclosed in the '986 patent is adapted to receive a sensor pack containing a plurality of blood glucose sensors. The sensor pack includes a circular base having a plurality of sensor retaining cavities, each of which hold an individual sensor. Each of the sensors has a generally flat, rectangular shape with a front testing end through which fluid is drawn so as to react with a reagent material in the sensor and an opposite rear, contact end.

The sensor instrument disclosed in the '986 patent includes an outer housing having an upper and a lower case that are pivotable with respect to each other so that the sensor pack can be positioned in the housing on an indexing disk disposed in the housing. With the sensor pack loaded in the housing, a slide latch on a slide actuator disposed on the upper case of the housing controls whether the movement of the slide actuator places the instrument in a display mode or in a testing mode. The instrument is placed into its display mode when the slide latch is moved laterally and the slide actuator is pushed away from its standby position. When in the display mode, a person using the instrument can view data displayed on a display unit in the upper case and/or input data into the instrument.

The instrument is in its testing mode when the slide latch is in its normal position and the slide actuator is pushed towards its testing position. As the slide actuator is moved towards its actuated position, the driver with the knife blade thereon moves toward the testing position of the feed mechanism and the disk drive arm travels in a straight, radially extending groove in the indexing disk such that the disk is not rotated as the feeding mechanism is moving towards its testing position. The knife blade is moved towards one of the sensor cavities in the sensor pack and pierces the foil covering the sensor cavity so as to engage the sensor disposed in the cavity. As the slide actuator and the driver are pushed toward the actuated position of the actuator, the knife blade ejects the sensor out from the sensor cavity and into a testing position near the testing end of the sensor housing.

Once the blood analyzing test is completed, the slide actuator is moved in the opposite direction towards its standby position so that the sensor can be removed from the dispensing instrument. The continued retraction of the driver causes the indexing disk drive arm to travel along a curvilinearly extending groove in the indexing disk, resulting in the rotation of the indexing disk. The rotation of the indexing disk results in the sensor pack being rotated so that the next sensor is positioned in alignment with the knife blade for the next blood glucose test that is to be performed.

Although the sensor instrument disclosed in the '986 patent overcomes many of the problems discussed above in connection with the use of individual sensors, some users have experienced difficulties in the operation and/or manipulation of the disclosed sensor instrument. For example, users with limited dexterity may find it difficult to remove a used sensor from the device. Because the used sensor contains blood or other fluids, the sensor should be disposed of immediately after the testing procedure is complete. Moreover, physical handling of the used sensor should be avoided to prevent the spreading of blood born diseases or other harmful contaminants. It is therefore desirable that the used sensor be removed from the device without being grasped or otherwise handled by the user.

In the device disclosed in the '986 patent, a used sensor is ordinarily discharged by sliding the slide latch away from the testing end of the device and simultaneously tipping the testing end of the device downwardly. This requires an awkward manipulation of the device that may be particularly difficult for users, particularly elderly users suffering from diabetes, which lack dexterity in their wrist, hand or fingers. As a result, many users may be tempted to grab the end of the used sensor to remove it from the device. It is therefore desirable to have an improved sensor dispensing instrument that utilizes a simplified method of discharging used sensors, and can be more easily manipulated by users with limited dexterity.

In addition, because the slide latch is manipulated during the testing procedure, and is used to place the device into the display mode, the user may inadvertently discharge the sensor from the testing position prior to conducting or completing the blood glucose test. For example, if the user accidentally slides the slide latch away from the testing end of the device during the middle of the testing procedure, the sensor may fall out of the device before the blood glucose test is complete. The user would then need to re-start the testing procedure to load a new sensor into the testing position. It is therefore desirable to have an improved sensor dispensing instrument that is less likely to inadvertently discharge sensors.

BRIEF SUMMARY OF THE INVENTION

Accordingly, an object of the present invention is to provide a new and improved sensor dispensing instrument for handling the sensors contained in a sensor pack of multiple sensors used in testing blood glucose. In particular, objects of the present invention are to provide a new and improved fluid sensor dispensing instrument handling device having an improved design and mechanism for discharging a sensor following the completion of the testing procedure, can be more easily manipulated by a user with limited wrist, hand or finger dexterity, reduces the inadvertent discharge of sensors, and which otherwise overcomes the problems or limitations discussed above.

In accordance with these and many other objects of the present invention, the present invention is embodied in a sensor dispensing instrument that is adapted to handle a sensor pack containing a plurality of sensors, each of the plurality of sensors being disposed in a sensor cavity on the sensor pack and enclosed by a protective foil covering. The sensor dispensing instrument is further adapted to perform a test using one of the sensors. The sensor dispensing instrument includes an outer housing having a front end and a rear end, and a sensor slot at the front end of the housing through which one of said sensors is disposed to conduct the test. The sensor dispensing instrument also includes a mechanical mechanism that has an indexing disk for supporting and rotating the sensor pack, an indexing disk drive arm for rotating the indexing disk, a knife blade assembly for puncturing the foil covering and ejecting one of the sensors from the sensor cavity and through the sensor slot, and a puller handle for moving the indexing disk drive arm and the knife blade assembly. The sensor dispensing instrument also includes a sensor actuator generally disposed adjacent to the sensor slot. The sensor actuator is adapted to engage with a sensor disposed in the sensor slot, to connect to contacts on the sensor, and to transmit electrical signals between the sensor and an electronics assembly disposed in the outer housing for performing the test and displaying test results. A sensor release is generally disposed on a surface of the outer housing. The sensor release is movable to disengage the sensor actuator from the sensor disposed in the sensor slot and permit the release or discharge of the sensor.

In the preferred embodiment, the mechanical mechanism also includes a movable disk drive pusher, with the indexing disk drive arm and the knife blade assembly being mounted on the disk drive pusher, and the puller handle being affixed to the rear end of the disk drive pusher. The sensor actuator is engaged by a front end of the disk drive pusher to cause the sensor actuator to engage the sensor disposed in the sensor slot. The sensor release engages the front end of the disk drive pusher to cause the sensor actuator to disengage from the sensor disposed in the sensor slot.

In accordance with another aspect of the present invention, the present invention is embodied in a method of operating a sensor dispensing instrument that is adapted to handle a sensor pack containing a plurality of sensors and to perform a test using one of the sensors, wherein the sensor dispensing instrument includes an outer housing having a sensor slot through which one of the sensors is disposed to conduct the test, a mechanical mechanism having an indexing disk for supporting and rotating the sensor pack, an indexing disk drive arm for rotating the indexing disk, a knife blade assembly for puncturing the foil covering and ejecting one of the sensors from the sensor cavity and through the sensor slot, and a puller handle for moving the indexing disk drive arm and the knife blade assembly, and a sensor release for engaging the drive pusher. The method comprises the steps of: a) grasping said puller handle when the puller handle is in the stand-by position; b) pulling the puller handle from the stand-by position to the extended position so as to rotate the indexing disk; c) pushing the puller handle from the extended position to the testing position so as to eject one of said sensors from the sensor cavity and through the sensor slot; d) performing the test by using the sensor disposed in the sensor slot; e) viewing the test results generated by the test on a liquid crystal display; and f) activating the sensor release to move the puller handle from the testing position to the stand-by position so as to cause the sensor to be released from the sensor slot.

BRIEF DESCRIPTION OF SEVERAL VIEWS OF THE DRAWINGS

The present invention, together with the above and other objects and advantages, can best be understood from the following detailed description of the embodiment of the invention illustrated in the drawing, wherein:

FIG. 1 is a top perspective view of a blood glucose sensor dispensing instrument embodying the present invention;

FIG. 2 is a bottom perspective view of the blood glucose sensor dispensing instrument of FIG. 1;

FIG. 3 is a perspective view of the blood glucose sensor dispensing instrument of FIG. 1 in the opened position showing the insertion of a sensor pack;

FIG. 4 is a perspective view of the blood glucose sensor dispensing instrument of FIG. 1 in the opened position showing a sensor pack loaded onto the indexing disk;

FIG. 5 is a top perspective view of the blood glucose sensor dispensing instrument of FIG. 1 shown with the button door in the open position;

FIG. 6 is a top perspective view of the blood glucose sensor dispensing instrument of FIG. 1 with the disk drive pusher in the extended position;

FIG. 7 is a top perspective view of the blood glucose sensor dispensing instrument of FIG. 1 with the disk drive pusher in the testing position with a sensor projecting from the sensor opening;

FIG. 8 is a top perspective view of a sensor for use with blood glucose sensor dispensing instrument of FIG. 1;

FIG. 9 is an exploded perspective view of a sensor pack for use with blood glucose sensor dispensing instrument of FIG. 1 showing the protective foil separated from the base portion of the sensor pack;

FIG. 13 is an exploded top perspective view of the component parts of the disk drive mechanism and indexing disk sub-assembly of the blood glucose sensor dispensing instrument of FIG. 1;

DETAILED DESCRIPTION OF THE INVENTION

Figure 10:
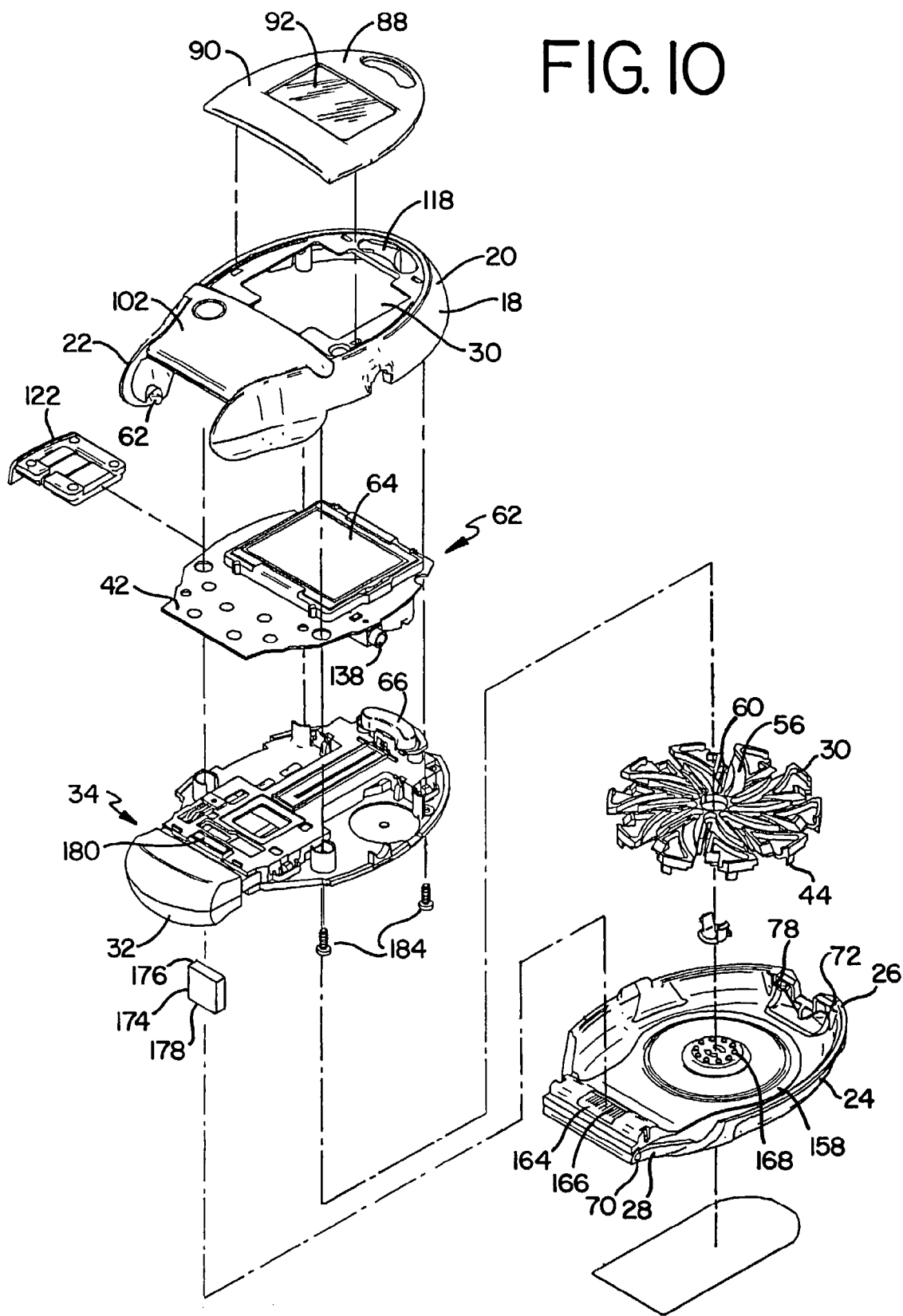
FIG. 10 is an exploded perspective view of the component sub-assemblies of blood glucose sensor dispensing instrument of FIG. 1.

Referring now more specifically to the drawings, therein is disclosed a blood glucose sensor dispensing instrument generally designated by the reference numeral 10 and embodying the present invention. The sensor dispensing instrument 10 includes an outer housing 12 having an upper case 18 and a lower case 24, the lower case 24 pivoting on the upper case 18. The upper case 18 is pivotable with respect to the lower case 24 in a clamshell fashion so that a sensor pack 300 (see FIGS. 3 and 4) can be positioned on an indexing disk 30 within the housing 12. With the sensor pack 300 so loaded in the housing 12, a puller handle 32 extending from a rear end 22 of the upper case 18 of the housing 12 can be moved to activate a disk drive mechanism, generally designated by the numeral 34 (see FIG. 10), to load a sensor 302 into a testing position on the front end 14 of the housing 12 (see FIG. 3).

It should be noted that the sensor dispensing instrument 10 of the present invention incorporates components that are similar in design and/or function as those described in U.S. Pat. No. 5,630,986, issued May 20, 1997, and entitled Dispensing Instrument For Fluid Monitoring Sensors. The contents of this patent are hereby incorporated by reference to avoid the unnecessary duplication of the description of these similar components.

The sensor pack 300 utilized by the sensor dispensing instrument 10 is of the type described in U.S. Pat. No. 5,575,403, issued Nov. 19, 1996, and entitled Dispensing Instrument For Fluid Monitoring Sensors, the contents of which are hereby incorporated by reference. In general, and as shown in FIGS. 8 and 9, the sensor pack 300 is adapted to house ten sensors 302, with one of the ten sensors 302 in each of ten separate sensor cavities 304. Each of the sensors 302 has a generally flat, rectangular shape extending from a front or testing end 306 to a back end 308. The front end 306 is angled so that it will puncture an unsevered portion of the protective foil 310 overlying the sensor cavity 304 as the sensor 302 is being forced out of the sensor cavity 304 by a knife blade 36 (to be described below). The front end 306 is also adapted to be placed into blood that is being analyzed. The back end 308 of the sensor 302 includes a small notch 312 that is engaged by the knife blade 36 as the knife blade 36 ejects the sensor 302 from the sensor cavity 304. Contacts 314 near the back end 308 of the sensor 302 are adapted to mate with metal contacts 38 on a sensor actuator 40 (to be described below) when the sensor 302 is in the testing position illustrated in FIG. 7. As a result, the sensor 302 is coupled to the electronic circuitry on the circuit board assembly 42 so that information generated in the sensor 302 during testing can be stored, analyzed and/or displayed.

As best seen in FIG. 8, each sensor 302 is provided with a capillary channel 316 that extends from the front or testing end 306 of the sensor 302 to biosensing or reagent material disposed in the sensor 302. When the testing end 306 of the sensor 302 is placed into fluid (for example, blood that is accumulated on a person's finger after the finger has been pricked), a portion of the fluid is drawn into the capillary channel 316 by capillary action. The fluid then chemically reacts with the reagent material in the sensor 302 so that an electrical signal indicative of the blood glucose level in the blood being tested is supplied to the contacts 314, and subsequently transmitted through the sensor actuator 40 to the circuit board assembly 42.

As best seen in FIG. 9, the sensor pack 300 comprises a circularly shaped base portion 318 covered by a sheet of protective foil 310. The sensor cavities 304 are formed as depressions in the base portion 318, with each of the sensor cavities 304 adapted to house an individual sensor 302. Each of the sensor cavities 304 has an inclined or sloped support wall 320 to guide the sensor 302 as the sensor 302 is ejected through the foil 310 and out of the sensor cavity 304.

Each of the sensor cavities 304 is in fluid communication with a desiccant cavity 322 formed by a small depression in the base portion 318. Desiccant material is disposed in each of the desiccant cavities 322 in order to insure that the sensor cavities 304 are maintained at an appropriate humidity level to preserve the reagent material in the sensor 302.

Notches 324 are formed along the outer peripheral edge of the base portion 318. The notches 324 are configured to engage pins 44 on the indexing disk 30 so that the sensor cavities 304 are in proper alignment with the indexing disk 30 when the sensor pack 300 is loaded into the sensor dispensing instrument 10. As will be explained in greater detail below, the sensor cavities 304 must be aligned with the knife slots 46 in the indexing disk 30 to permit the knife blade 36 to engage, eject and push one of the sensors 302 into a testing position on the front end 14 of the housing 12.

The sensor pack 300 further comprises a conductive label 326 on the central portion of the base portion 318. As will be explained below, the conductive label 326 provides calibration and production information about the sensor pack 300 that can be sensed by calibration circuitry in the sensor dispensing instrument 10.

To operate the sensor dispensing instrument 10, the puller handle 32 is first manually pulled from a standby position (FIG. 1) adjacent the rear end 16 of the housing 12 to an extended position (FIG. 6) away from the rear end 16 of the housing 12. The outward movement of the puller handle 32 causes the disk drive mechanism 34 to rotate the sensor pack 300 and place the next sensor 302 in a standby position prior to being loaded into a testing position. The outward movement of the puller handle 32 also causes the sensor dispensing instrument 10 to turn ON (i.e., the electronic circuitry on the circuit board assembly 42 is activated).

As will be described in greater detail below, the disk drive mechanism 34 includes a disk drive pusher 48 on which an indexing disk drive arm 50 is mounted (see FIGS. 13 and 14). The indexing disk drive arm 50 comprises a cam button 52 disposed at the end of a plate spring 54. The cam button 52 is configured to travel in one of a plurality of curvilinearly extending grooves 56 on the upper surface of the indexing disk 30. As the puller handle 32 is manually pulled from a standby position adjacent the rear end 16 of the housing 12 to an extended position away from the rear end 16 of the housing 12, the disk drive pusher 48 is pulled laterally towards the rear end 22 of the upper case 18. This causes the cam button 52 on the indexing disk drive arm 50 to travel along one of the curvilinearly extending grooves 56 so as to rotate the indexing disk 30. The rotation of the indexing disk 30 causes the sensor pack 300 to be rotated so that the next one of the sensor cavities 304 is placed in a standby position.

The puller handle 32 is then manually pushed inwardly from the extended position (FIG. 6) back past the standby position (FIG. 1) and into a testing position (FIG. 7). The inward movement of the puller handle 32 causes the disk drive mechanism 34 to remove a sensor 302 from the sensor pack 300 and place the sensor 302 into a testing position on the front end 14 of the housing 12.

As will be described in greater detail below, the disk drive mechanism 34 includes a knife blade assembly 58 that is pivotally mounted to the disk drive pusher 48 (see FIGS. 13 and 14). As the puller handle 32 is manually pushed from the extended position to the testing position, the disk drive pusher 48 is pushed laterally towards the testing or front end 20 of the upper case 18. This causes the knife blade assembly 58 to pivot downwardly so that a knife blade 36 on the end of the knife blade assembly 58 pierces a portion of the protective foil 310 covering one of the sensor cavities 304 and engages the sensor 302 in the sensor cavity 304. As the disk drive pusher 48 continues to move towards the front end 20 of the upper case 18, the knife blade assembly 58 forces the sensor 302 out of the sensor cavity 304 and into a testing position at the front end 14 of the housing 12.

While the disk drive pusher 48 is being pushed from the extended position to the testing position, the cam button 52 on the indexing disk drive arm 50 travels along one of the radially extending grooves 60 to prevent the indexing disk 30 from rotating. Similarly, while the disk drive pusher 48 is being pulled from the standby position to the extended position, the knife blade assembly 58 is in a retracted position so as to not interfere with the rotation of the indexing disk 30.

After the sensor 302 has been completely ejected from the sensor cavity 304 and pushed into a testing position projecting out from the front end 14 of the housing 12, the disk drive pusher 48 engages and forces a sensor actuator 40 against the sensor 302 to thereby maintain the sensor 302 in the testing position. The sensor actuator 40 engages the sensor 302 when the puller handle 32 is pushed past the standby position and into the testing position. The sensor actuator 40 couples the sensor 302 to an electronics assembly 62 disposed in the upper case 18. The electronics assembly 62 includes a microprocessor or the like for processing and/or storing data generated during the blood glucose test procedure, and displaying the data on a liquid crystal display 64 in the sensor dispensing instrument 10.

Once the blood analyzing test is completed, a button release 66 on the upper case 18 is depressed so as to disengage the sensor actuator 40 and release the sensor 302. Depressing the button release 66 causes the disk drive pusher 48 and the puller handle 32 to move from the testing position back to the standby position. At this point, the user can turn the sensor dispensing instrument 10 OFF by depressing the button 96 on the upper case 18, or by allowing the sensor dispensing instrument 10 automatically turn OFF pursuant a timer on the electronics assembly 62.

As seen in FIGS. 1-7 and 10-12, the upper case 18 and the lower case 24 of the sensor dispensing housing 12 are complementary, generally oval shaped hollow containers that are adapted to be pivoted with respect to each other about pivot pins 68 extending outwardly in the rear end 22 of the upper case 18 into pivot holes 70 in a rear section 28 of the lower case 24. The upper case 18 and the lower case 24 are maintained in their closed configuration by a latch 72 that is pivotally mounted in a front section 26 of the lower case 24 by pins 74 that extend inwardly into pivot holes 76 in the latch 72 (see FIG. 12). The latch 72 has recesses 78 that are configured to mate with hooks 80 on the upper case 18 to secure the upper case 18 and the lower case 24 in their closed configuration. The latch 72 is biased in a vertical or closed position by a latch spring 82. The ends 84 of the latch spring 82 are secured in slots 86 on the inside of the lower case 24. When the latch 72 is pivoted against the biasing force of the latch spring 82, the hooks 80 on the upper case 18 disengage from the recesses 78 to permit the upper case 18 and the lower case 24 to open.

Figure 11:
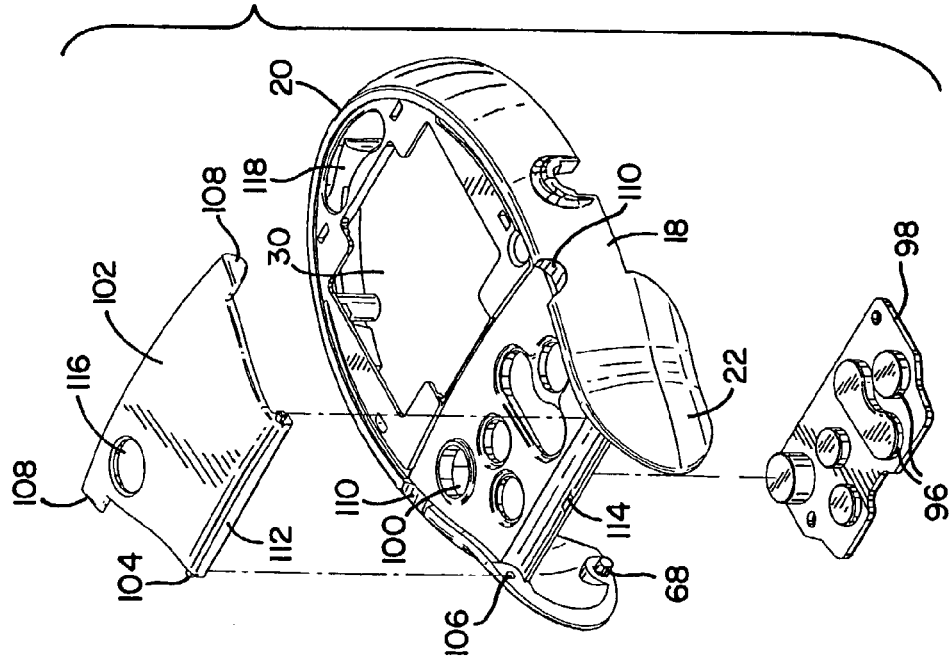
FIG. 11 is an exploded perspective view of the component parts of the upper case sub-assembly of the blood glucose sensor dispensing instrument of FIG. 1.

As seen in FIGS. 1, 5-7 and 10-11, the upper case 18 includes a rectangular opening 30 through which a liquid crystal display 64 is visible below. The liquid crystal display 64 is visible through a display lens 88 that is affixed to upper surface of the upper case 18. In the preferred embodiment shown, the display lens 88 has an opaque portion 90 and a transparent portion 92, the transparent portion 92 being coincident with the display area of liquid crystal display 64. The liquid crystal display 64 is a component of the electronics assembly 62, and is coupled to the circuit board assembly 42 via elastomeric connectors 94 (see FIG. 16). The liquid crystal display 64 displays information from the testing procedure and/or in response to signals input by the buttons 96 on the upper case 18. For example, the buttons 96 can be depressed to recall and view the results of prior testing procedures on the liquid crystal display 64. As best seen in FIG. 11, the buttons 96 are part of a button set 98 that is attached to the upper case 18 from below so that the individual buttons 96 project upwardly through button openings 100 in the upper case 18. When pressed, the buttons 96 are electrically connected to the circuit board assembly 42.

As best seen in FIGS. 1, 5 and 11, a button door 102 is pivotally connected to the upper case 18 by a pair of pins 104 projecting outwardly from either side of the button door 102 that engage holes 106 on the side walls of the upper case 18. The button door 102 also comprises a pair of ears 108 that fit into recesses 110 in the side walls of the upper case 18 when the button door 102 is closed. The ears 108 extend slightly beyond the side walls of the upper case 18 so that they can be grasped by the user to open the button door 102. A pivot edge 112 of the button door 102 engages a tab 114 on the upper surface of the upper case 18. The tab 114 rubs against the pivot edge 112 in such a manner so as to bias the button door 102 in either a closed or fully open position. In the preferred embodiment shown, the button door 102 has an opening 116 that permits one of the buttons 96 (e.g., an On/Off button) to be accessed when the button door 102 is closed (see FIG. 1). This permits dedicated, but seldom or lesser used buttons 96 to be concealed underneath the button door 102, thereby simplifying the learning curve and daily operation of the sensor dispensing instrument 10 for the user.

The upper case 18 also contains an opening 118 for the button release 66, which projects upwardly through the upper case 18. As will be described in more detail below, the button release 66 is depressed to disengage the sensor actuator 40 and release a sensor 302 from the testing position.

The upper case 18 also contains an opening 120 for a battery tray assembly 122. The battery tray assembly 122 includes a battery tray 124 in which a battery 126 is disposed. The batter tray assembly 122 is inserted into the opening 120 in the side of the upper case 18. When so inserted, the battery 126 engages battery contacts 128 and 130 on the circuit board assembly 42 so as to provide power for the electronics within the instrument 10, including the circuitry on the circuit board assembly 42 and the liquid crystal display 64. A tab 132 on the lower case 24 is configured to engage a slot 134 in the battery tray assembly 122 so as to prevent the battery tray assembly 122 from being removed from the sensor dispensing instrument 10 when the upper case 18 and the lower case 24 are in the closed configuration.

Figure 16:
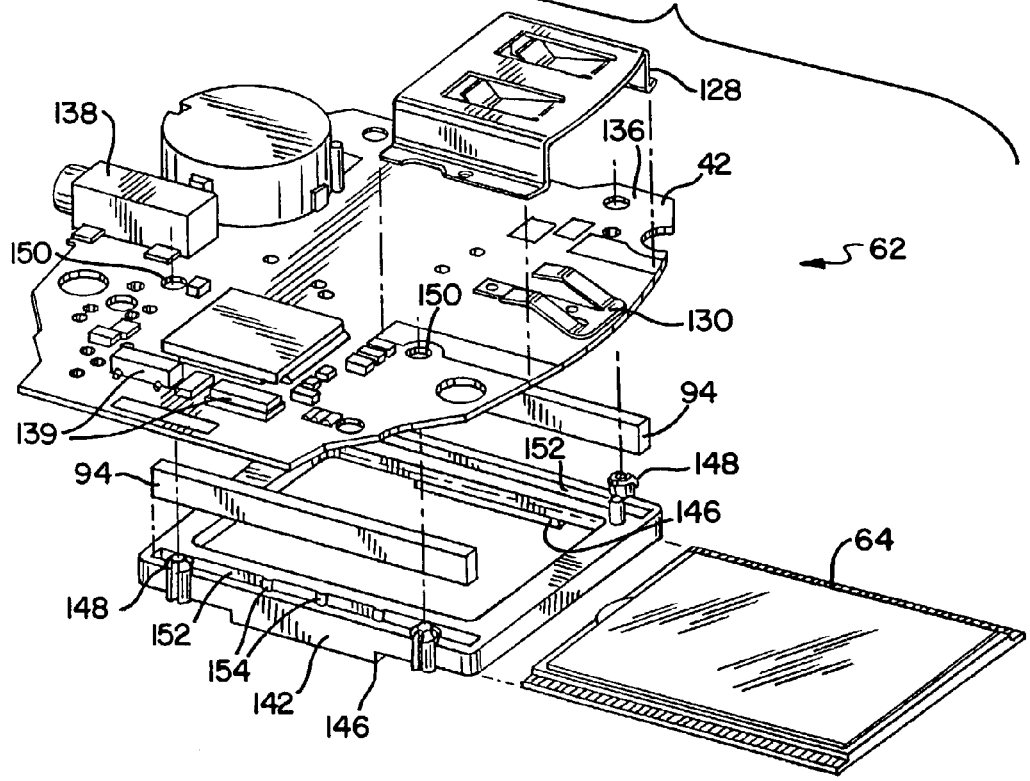
FIG. 16 is an exploded perspective view of the component parts of the electronics assembly of the blood glucose sensor dispensing instrument of FIG. 1.
Figure 17:
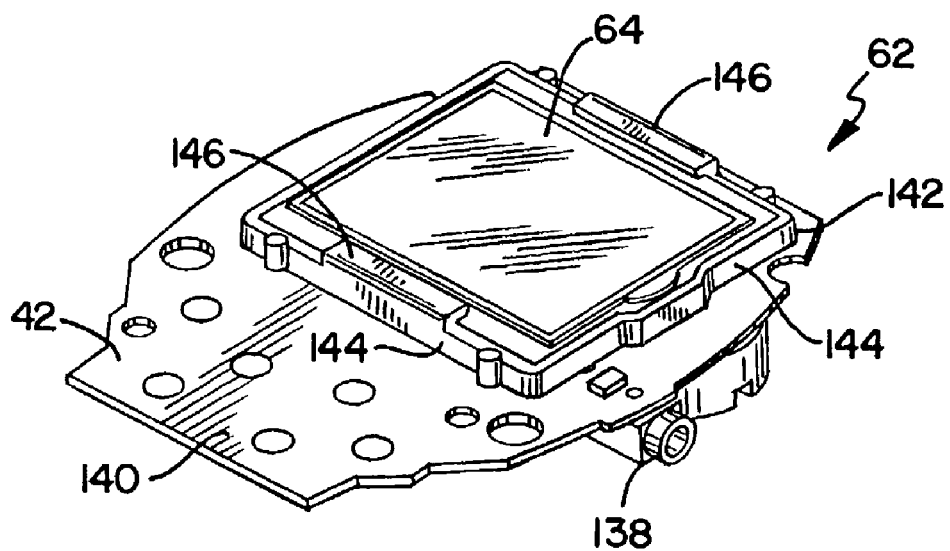
FIG. 17 is a top perspective view of the electronics sub-assembly of the blood glucose sensor dispensing instrument of FIG. 1.
Figure 18:
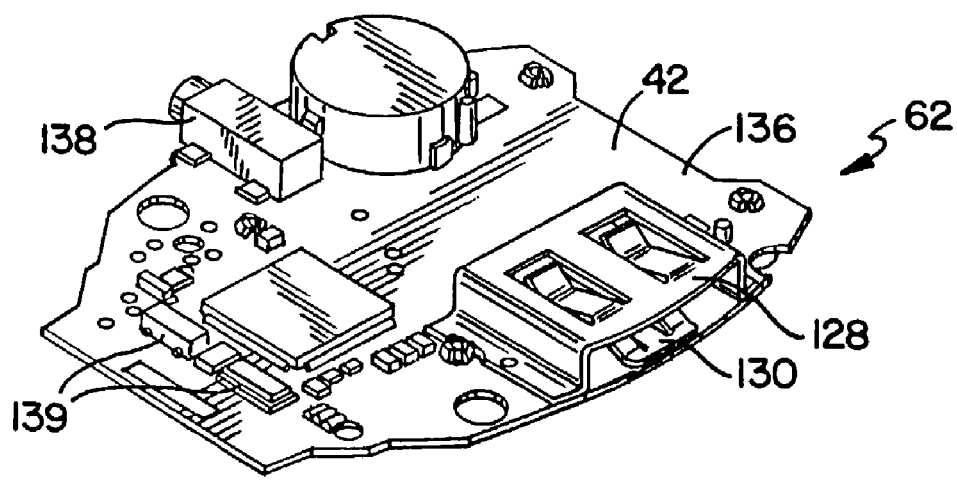
FIG. 18 is a bottom perspective view of the electronics sub-assembly of the blood glucose sensor dispensing instrument of FIG. 1.

An electronics assembly 62 is affixed to the upper inside surface of the upper case 18. As best seen in FIGS. 16-18, the electronics assembly 62 comprises a circuit board assembly 42 on which various electronics and electrical components are attached. A positive battery contact 128 and a negative battery contact 130 are disposed on the bottom surface 136 (which is the upwardly facing surface as viewed in FIGS. 16 and 18) of the circuit board assembly 42. The battery contacts 128 and 130 are configure to electrically connect with the battery 126 when the battery tray assembly 122 is inserted into the side of the upper case 18. The bottom surface 136 of the circuit board assembly 42 also includes a communication interface 138. The communication interface 138 permits the transfer of testing or calibration information between the sensor dispensing instrument 10 and another device, such as a personal computer, through standard cable connectors (not shown). In the preferred embodiment shown, the communication interface 138 is a standard serial connector. However, the communication interface 138 could alternatively be an infra-red emitter/detector port, a telephone jack, or radio frequency transmitter/receiver port. Other electronics and electrical devices, such as memory chips for storing glucose test results or ROM chips for carrying out programs are likewise included on the bottom surface 136 and the upper surface 140 of the circuit board assembly 42.

A liquid crystal display 64 is affixed to the upper surface 140 (upwardly facing surface in FIG. 17) of the circuit board assembly 42. The liquid crystal display 64 is held by a snap-in display frame 142. The snap-in display frame 142 includes side walls 144 that surround and position the liquid crystal display 64. An overhang 146 on two of the side walls 144 holds the liquid crystal display 64 in the snap-in display frame 142. The snap-in display frame 142 includes a plurality of snap fasteners 148 that are configured to engage mating holes 150 on the circuit board assembly 42. The liquid crystal display 64 is electrically connected to the electronics on the circuit board assembly 42 by a pair of elastomeric connectors 94 disposed in slots 152 in the snap-in display holder 142. The elastomeric connectors 94 generally comprise alternating layers of flexible conductive and insulating materials so as to create a somewhat flexible electrical connector. In the preferred embodiment shown, the slots 152 contain a plurality of slot bumps 154 that engage the sides of the elastomeric connectors 94 to prevent them from falling out of the slots 152 during assembly.

As set forth in detail in the U.S. Patent Application entitle Snap-in Display Frame, which is being filed together with the present application, the snap-in display frame 142 eliminates the screw-type fasteners and metal compression frames that are typically used to assemble and attach a liquid crystal display 64 to an electronic device. In addition, the snap-in display frame 142 also permits the liquid crystal display 64 to be tested prior to assembling the liquid crystal display 64 to the circuit board assembly 42.

The button set 98 also mates to the upper surface 140 of the circuit board assembly 42. As mentioned above, the button set 98 comprises several individual buttons 96 that are depressed to operate the electronics of the sensor dispensing instrument 10. For example, the buttons 96 can be depressed to activate the testing procedure of the sensor dispensing instrument 10. The buttons 96 can also be depressed to recall and have displayed on the liquid crystal display 64 the results of prior testing procedures. The buttons 96 can also be used to set and display date and time information, and to activate reminder alarms which remind the user to conduct a blood glucose test according to a predetermined schedule. The buttons 96 can also be used to activate certain calibration procedures for the sensor dispensing instrument 10.

The electronics assembly 62 further comprises a pair of surface contacts 139 on the bottom surface 136 of the circuit board assembly 42 (see FIGS. 16 and 18). The surface contacts 139 are configured so as to be contacted by one or more fingers 143 on the cover mechanism 188, which in turn are configured to be engaged by a pair of ramp contacts 141 on the disk drive pusher 48 (see FIGS. 6 and 13). Movement of the puller handle 32 causes the ramp contacts 141 to push the fingers 143 into contact with one or both of the surface contacts 139 so as to communicate the position of the puller handle 32 to the electronics assembly 62. In particular, movement of the puller handle 32 from the stand-by or testing positions to the extended position will turn the sensor dispensing instrument ON. In addition, if the housing 12 is opened while the puller handle 32 is in the extended position, an alarm will be activated to warn the user that the knife blade 36 may be in the extended position.

It should be noted that the design and configuration of the electronics assembly 62 permits the assembly and testing of the electronics and electrical components prior to assembly of the electronics assembly 62 to the upper case 18 of the sensor dispensing instrument 10. In particular, the liquid crystal display 64, the button set 98, the battery contacts 128 and 130, and the other electronics and electrical components can each be assembled to the circuit board assembly 42 and tested to verify that these components, and the electrical connections to these components, are working properly. Any problem or malfunction identified by the testing can then be corrected, or the malfunctioning component can be discarded, prior to assembling the electronics assembly 62 to the upper case 18 of the sensor dispensing instrument 10.

Figure 12:
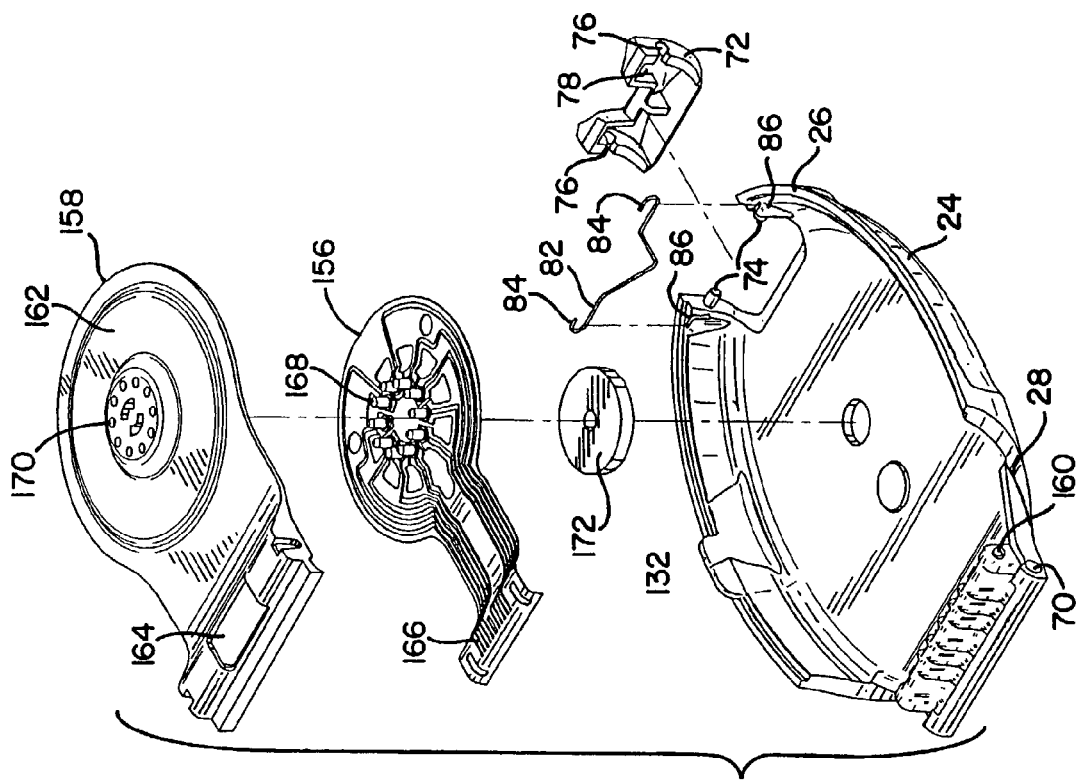
FIG. 12 is an exploded perspective view of the component parts of the lower case sub-assembly of the blood glucose sensor dispensing instrument of FIG. 1.

As mentioned above, the sensor dispensing instrument 10 includes calibration circuitry for determining calibration and production information about the sensor pack 300. As best seen in FIG. 12, the calibration circuitry comprises a flex circuit 156 located in the lower case 24. The flex circuit 156 is held in position in the lower case 24 by an autocal disk 158 that is connected to the rear section 28 of the lower case 24 by a pair of pins 160. The autocal disk 158 has a raised central portion 162 configured to engage the sensor cavities 304 on the sensor pack 300 so as to hold the sensor pack 300 against the indexing disk 30. The autocal disk 158 also has an open area 164 located between the pins 160 to expose contacts 166 on the flex circuit 156.

The flex circuit 156 comprises a plurality of probes 168 that extend upwardly from the flex circuit 156 through holes 170 in the inner region of the autocal disk 158. These probes 168 are connected to the contacts 166 on the end of the flex circuit 156. When the sensor dispensing instrument 10 is closed with the lower case 24 latched to the upper case 18, the probes 168 make contact with a conductive label 326 on the sensor pack 300 being used in the sensor dispensing instrument 10. A foam pad 172 is positioned below the flex circuit 156 to provide a biasing force to assure that the probes 168 press against the conductive label 326 with a force sufficient to make an electrical connection. The foam pad 172 also provides a cushioning force so that the probes 168 can move independently with respect to each other as the sensor pack 300 is being rotated by the indexing disk 30. As a result, information, such as calibration and production data, contained on the conductive label 326 can be transmitted via the probes 168 to the flex circuit 156, which in turn couples the data to the electronic circuitry on the circuit board assembly 42 via an elastomeric connector 174. This information can then be used by the electronics assembly 62 to calibrate the sensor dispensing instrument 10, or can be displayed on the liquid crystal display 64.

As best seen in FIG. 10, the elastomeric connector 174 is made of layers of silicon rubber extending from a top edge 176 to a bottom edge 178 with alternate layers having conductive materials dispersed therein to connect contacts on the top edge 176 to contacts on the bottom edge 178. When the upper case 18 and the lower case 24 are closed, the elastomeric connector 174 is compressed in the direction between the edges 176 and 178 such that the contacts along the top edge 176 engage electronic circuitry on the circuit board assembly 42 in the upper case 18, and the contacts along the bottom edge 178 engage the contacts 166 on the flex circuit 156 in the lower case 24. With the elastomeric connector 174 so compressed, low voltage signals can be readily transmitted between the circuit board assembly 42 and the flex circuit 156 through the elastomeric connector 174.

The elastomeric connector 174 is held in position by a slotted housing 180 on the guide block 182. In the preferred embodiment shown, the slotted housing 180 has a serpentine cross-section configured to allow the connector 174 to compress when the upper case 18 and the lower case 24 are closed, while still holding the elastomeric connector 174 when the upper case 18 and the lower case 24 are open. Alternatively, the slotted housing 180 may include inwardly projecting ridges that engage the sides of the connector 174.

The disk drive mechanism 34 is affixed to the upper inside surface of the upper case 18. As best seen in FIG. 10, the disk drive mechanism 34 is attached to the upper case by a plurality of mounting screws 184 that engage posts (not shown) on the upper inside surface of the upper case 18. The mounting screws 184 also pass through and secure the electronics assembly 62, which is disposed between the disk drive mechanism 34 and the upper case 18.

Although the disk drive mechanism 34 will be described in greater detail below, it should be noted that the disk drive mechanism 34 is configured so as to permit the assembly and testing of its operation prior to mounting the disk drive mechanism 34 to the upper inside surface of the upper case 18. In other words, the disk drive mechanism 34 has a modular design that can be tested prior to final assembly of the sensor dispensing instrument 10.

Figure 14:
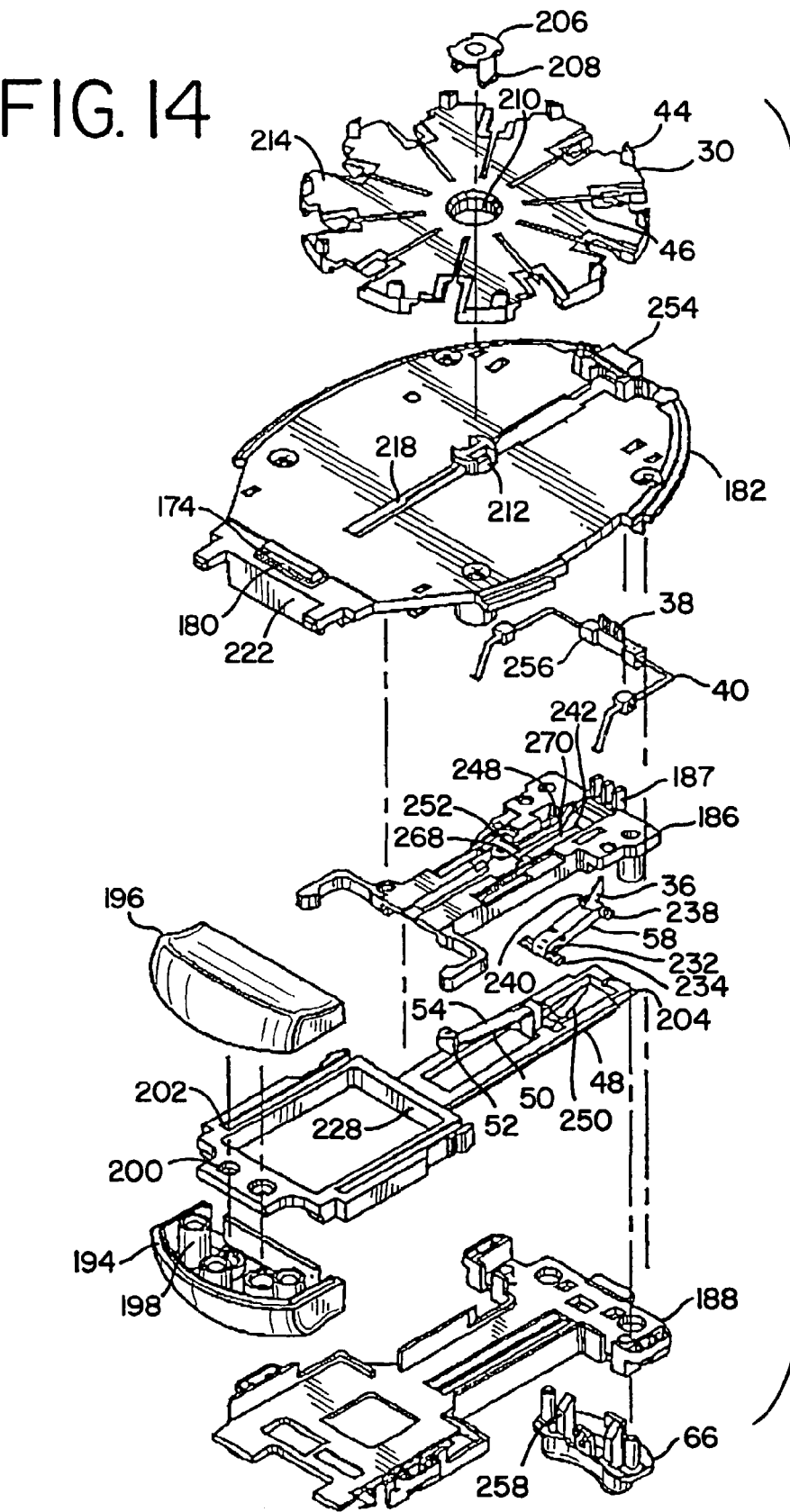
FIG. 14 is an exploded bottom perspective view of the component parts of the disk drive mechanism and indexing disk sub-assembly of the blood glucose sensor dispensing instrument of FIG. 1.
Figure 15:
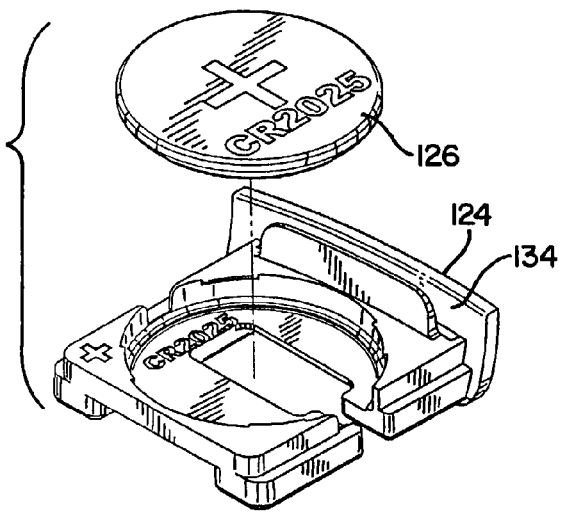
FIG. 15 is an exploded perspective view of the component parts of the battery tray sub-assembly of the blood glucose sensor dispensing instrument of FIG. 1.

As best seen in FIGS. 13 and 14, the disk drive mechanism 34 comprises a guide block 182, a sensor actuator 40, a housing guide 186, a disk drive pusher 48, an indexing disk drive arm 50, a knife blade assembly 58, a puller handle 32, a cover mechanism 188, and a button release 66. The housing guide 186 is fixed to the upper surface 190 (as viewed in FIG. 13) of the guide block 182 by one or more pins 192. The disk drive pusher 48 is supported on the housing guide 186 and the guide block 182 in such a manner as to permit the disk drive pusher 48 to slide laterally relative to the housing guide 186 and the guide block 182. The knife blade assembly 58 is pivotally connected to the underside of the disk drive pusher 48, and is guided by the housing guide 186 and the guide block 182. The indexing disk drive arm 50 is also connected to the disk drive pusher 48, and is partially guided by the guide block 182. The puller handle 32 comprises an upper puller handle 194 and a lower puller handle 196 connected to each other by snap-press fittings 198 that pass through holes 200 in the rear end 202 of the disk drive pusher 48. In the preferred embodiment shown, the upper puller handle 194 and the lower puller handle 196 each have a concaved, textured outer surface (i.e., the top and bottom surfaces of the puller handle 32) to facilitate gripping of the puller handle 32 between the thumb and finger of the user's hand. The cover mechanism 188 is affixed to the guide block 182 with the disk drive pusher 48 and the housing guide 186 disposed therebetween. The sensor actuator 40 is attached to the guide block 182 and is engaged by the front end 204 of the disk drive pusher 48 when the disk drive pusher 48 is in the testing position. The button release 66 is slidably connected to the cover mechanism 188 so as to engage the front end 204 of the disk drive pusher 48 when the disk drive pusher 48 is in the testing position.

In addition, an indexing disk 30 is rotatably secured to the disk drive mechanism 34 by a retainer disk 206 connected through the indexing disk 30 and into guide block 182. As best seen in FIG. 14, the retainer disk 206 has a pair of latch arms 208 that extend through a central hole 210 in the indexing disk 30 and latch into an opening 212 in the guide block 182. As mentioned above, the indexing disk 30 includes a plurality of pins 44 protruding from the lower surface 214 thereof. These pins 44 are configured to engage notches 324 on the sensor pack 300 (see FIG. 4) so as to align and rotate the sensor pack 300 in accordance with the position of the indexing disk 30. Hence, the pins 44 and the notches 324 have the dual purpose of retaining the sensor pack 300 on the indexing disk 30 so that the sensor pack 300 will rotate with the indexing disk 30 and of positioning the sensor pack 300 in proper circumferential alignment relative to the indexing disk 30.

As previously indicated, the disk drive pusher 48 is pulled away from the rear end 16 of the housing 12 (away from the testing end 14) by the user manually exerting a pulling force on the puller handle 32 to move the handle 32 from the standby position to the extended position. As the puller handle 32 is pulled away from the rear end 22 of the upper case 18, the disk drive pusher 48 is guided in a lateral direction by the guide block 182, the housing guide 186, and the cover mechanism 188. As the disk drive pusher 48 slides towards the rear end 22 on the upper case 18, the indexing disk drive arm 50 causes the indexing disk 30 to rotate.

The indexing disk drive arm 50 extends rearwardly from the disk drive pusher 48. The indexing disk drive arm 50 includes a plate spring 54 made of spring type material such as stainless steel so as to bias the arm 50 outwardly from the disk drive pusher 48. A cam button 52 is affixed to the distal end of the arm 50, and is configured to engage the upper surface 216 (as viewed in FIG. 13) of the indexing disk 30. In particular, the indexing disk drive arm 50 is bent so as to protrude downwardly through a slot 218 in the guide block 182 such that the cam button 52 projects outwardly from the surface thereof. The slot 218 is designed such that the indexing disk drive arm 50 and the cam button 52 can move along the slot 218 as the disk drive pusher 48 is moved back and forth during the testing procedure. The slot 218 also prevents the indexing disk drive arm 50 from moving sideways with respect to the disk drive pusher 48 (i.e., it provides lateral support to the indexing disk drive arm 50).

As best seen in FIG. 13, the upper surface 216 of the indexing disk 30 comprises a series of radially extending grooves 60 and a plurality of curvilinearly extending grooves 56. The cam button 52 is configured to ride along these grooves 56 and 60 during the movement of the disk drive pusher 48. As the disk drive pusher 48 slides towards the rear end 22 of the upper case 18, the cam button 52 moves along one of the curvilinearly extending grooves 56. This causes the indexing disk 30 to rotate. In the preferred embodiment shown, there are ten radially extending grooves 60 and ten curvilinearly extending grooves 56 equally spaced about the circumference of the indexing disk 30, with each radially extending groove 60 being disposed between a pair of curvilinearly extending grooves 56. Accordingly, the movement of the disk drive pusher 48 towards the rear end 22 on the upper case 18 results in a $1/10^{th}$ rotation of the indexing disk 30.

As the puller handle 32 is pulled away from the rear end 16 of the housing 12 to a fully extended position, the cam button 52 passes over an outer step 220 that separates the outer end 222 of the curvilinearly extending groove 56 from the adjacent radially extending groove 60. The outer step 220 is formed by the difference in depth between the outer end 222 of the curvilinearly extending groove 56 and the outer end 224 of the adjacent radially extending groove 60. In particular, the outer end 224 of the radially extending groove 60 is deeper than the outer end 222 of the curvilinearly extending groove 56. Thus, when the cam button 52 moves from the curvilinearly extending groove 56 into the adjacent radially extending groove 60, the biasing force of the plate spring 54 of the indexing disk drive arm 50 causes the cam button 52 to travel downwardly past the outer step 220. The outer step 220 prevents the cam button 52 from re-entering the outer end 222 of the curvilinearly extending groove 56 when the direction of travel of the disk drive pusher 48 is reversed (as will be explained below).

Rotation of the indexing disk 30 causes the sensor pack 300 to likewise rotate so that the next available sensor cavity 304 is placed in a standby position adjacent to the testing end 14 of the housing 12. The sensor pack 300 rotates with the indexing disk 30 because of the engagement of the notches 324 on the sensor pack 300 by the pins 44 on the indexing disk 30. As explained above, each sensor cavity 304 contains a disposable sensor 302 that is used during the glucose testing procedure.

Further rearward movement of the disk drive pusher 48 is prevented by a rear wall 226 on the guide block 182. In the preferred embodiment shown, the rear wall 226 includes a slotted housing 180 for holding the elastomeric connector 174 that connects the electronics assembly 62 to the flex circuit 156 disposed in the lower case 24. An interior edge 228 of the disk drive pusher 48 engages the rear wall 226 on the guide block 182 when the disk drive pusher 48 is in the fully extended position (see FIG. 6).

From the fully extended position, the puller handle 32 is then manually pushed inwardly back past the standby position (FIG. 1) and into a testing position (FIG. 7). As previously indicated, the inward movement of the puller handle 32 causes the disk drive mechanism 34 to remove a sensor 302 from the sensor pack 300 and place the sensor 302 into a testing position.

As best seen in FIGS. 13 and 14, the disk drive mechanism 34 includes a knife blade assembly 58 that is pivotally mounted to the disk drive pusher 48. The knife blade assembly 58 comprises a swing arm 230 having a first end 232 that is pivotally connected to the disk drive pusher 48 by a pair of pivot pins 234. A knife blade 36 is connected to the second end 236 of the swing arm 230. The second end 236 of the swing arm 230 also includes a first cam follower 238 and a second cam follower 240, each in the shape of a transversely extending post. The first cam follower 238 is configured to follow a pathway formed on one side of the knife blade assembly 58 by the guide block 182, the housing guide 186, and the cover mechanism 188. In particular, this pathway is formed by a cam projection 242 on the housing guide 186 that forms an upper pathway 244 between the cam projection 242 and the cover mechanism 188 and a lower pathway 246 between the cam projection 242 and the guide block 182. When the first cam follower 238 is disposed in the upper pathway 244, the knife blade 36 is in the retracted position. On the other hand, when the first cam follower 238 is disposed in the lower pathway 246, then the knife blade 36 is in the extended position. The upper pathway 244 and the lower pathway 246 are connected together at both ends of the cam projection 242 so as to form a continuous loop about which the first cam follower 238 can travel.

The second cam follower 240 engages a cam spring 248 attached to the housing guide 186. As will be explained below, the cam spring 248 guides the knife blade assembly 58 from the lower pathway 246 to the upper pathway 244 when the disk drive pusher 48 is initially pulled rearward from standby position towards the extended position. The disk drive pusher 48 also comprises a spring 250 for biasing the knife blade 36 towards the extended position when the disk drive pusher 48 is initially pushed forward from the extended position towards the testing position. In the preferred embodiment shown, the spring 250 comprises a plate spring that presses against the upper side of the swing arm 230.

As the puller handle 32 is manually pushed from the extended position to the testing position, the disk drive pusher 48 is pushed laterally towards the testing or front end 14 of the housing 12. As the disk drive pusher 48 begins to move forward, the spring 250 biases the swing arm 230 downwardly towards the indexing disk 30 so that the first cam follower 238 engages a sloped surface 252 on the interior end 268 of the cam projection 242 and is forced into the lower pathway 246. This causes the knife blade 36 to assume an extended position whereby the knife blade 36 projects outwardly through a knife slot 46 in the indexing disk 30 to pierce the protective foil 310 covering one of the sensor cavities 304 and engage the notch 312 on the back end 308 of the sensor 302 contained therein. As the disk drive pusher 48 continues to move towards the front end 20 of the upper case 18, the first cam follower 238 continues along the lower pathway 246, thereby causing the knife blade 36 to remain in the extended position projecting through the knife slot 46 so that it will travel along the knife slot 46 and push the sensor 302 forward out of the sensor cavity 304 and into a testing position at the front end 14 of the housing 12. The sensor 302 is in the testing position when the front end 306 of the sensor 302 projects out of the sensor opening 254 formed on the front end of the guide block 182. While in the testing position, the sensor 302 is prevented from being pushed back through the sensor opening 254 by the engagement of the knife blade 36 against the notch 312 on the back end 308 of the sensor 302.

As the disk drive pusher 48 reaches the testing position, the front end 204 of the disk drive pusher 48 simultaneously engages the sensor actuator 40 and the button release 66. In particular, the front end 204 of the disk drive pusher 48 engages and pushes the button release 66 outwardly so as to project upwardly from the upper surface of the upper case 18. At the same time, the front end 204 of the disk drive pusher 48 engages a contact pad 256 on the sensor actuator 40 so as to force the sensor actuator 40 downward. This downward motion causes a pair of metal contacts 38 on the sensor actuator 40 to project into the sensor opening 254 on the guide block 182 and engage the contacts 314 on the sensor 302 for the glucose testing procedure. The metal contacts 38 also apply a frictional force to the sensor 302 so that the sensor 302 does not prematurely fall out of the sensor opening 254 prior to completion of the glucose testing procedure. In the preferred embodiment shown, the metal contacts 38 are somewhat flexible and are made of stainless steel. The housing guide 186 includes support ribs 187 disposed adjacent to the metal contacts 38 so as to prevent the metal contacts 38 from bending. As explained above, the metal contacts 38 permit the transmission of electrical signals between the sensor 302 and the electronics assembly 62 during the glucose testing procedure.

When the glucose testing procedure is complete, the button release 66 is depressed to release the sensor 302 from the testing position. The button release 66 has a sloped contact surface 258 that engages the front end 204 of the disk drive pusher 48 at an angle. As the button release 66 is depressed, the sloped contact surface 258 slides along the front end 204 of the disk drive pusher 48, thereby causing the disk drive pusher 48 to move rearward from the testing position and into the standby position. In the preferred embodiment shown, the disk drive pusher 48 is moved laterally a distance of 0.080 inches. The movement of the disk drive pusher 48 to the standby position also causes the front end 204 of the disk drive pusher 48 to disengage from the contact pad 256 on the sensor actuator 40, thereby allowing the sensor actuator 40 to move away from and disengage the sensor 302. The sensor 302 can then be removed by tipping the front end 14 of the sensor dispensing instrument 10 downwardly.

As mentioned above, when the disk drive pusher 48 is pushed from the extended position towards the testing position, the cam button 52 on the indexing disk drive arm 50 travels along one of the radially extending grooves 60 to prevent the indexing disk 30 and the sensor pack 300 from rotating. The radially extending groove 60 includes a sloped portion 260 that changes the depth of the groove 60. In particular, the sloped portion 260 decreases the depth of the radially extending groove 60 so that the middle portion of the radially extending groove 60 is shallower than the curvilinearly extending grooves 56. The radially extending groove 60 also comprises an inner step 262 near its inner end 264 (i.e., near the center of the indexing disk 30). The inner step 262 is formed along the juncture of the inner end 264 of the radially extending groove 60 and the inner end 266 of the curvilinearly extending groove 56. As the disk drive pusher 48 is pushed from the extended position towards the testing position, the cam button 52 travels up the sloped portion 260 of the radially extending groove 60, past the inner step 262, and into the adjacent curvilinearly extending groove 56. The biasing force of the plate spring 54 of the indexing disk drive arm 50 causes the cam button 52 to travel downwardly past the inner step 262. The inner step 262 prevents the cam button 52 from re-entering the radially extending groove 60 when the direction of travel of the disk drive pusher 48 is reversed (as explained above in connection with the outward movement of the disk drive pusher 48).

As the disk drive pusher 48 reaches the testing position, the first cam follower 238 passes the exterior end 270 of the cam projection 242. At the same time, the second cam follower 240 passes over the end of the cam spring 248, which retracts upwardly and out of the way as the first cam follower 238 nears the exterior end 270 of the cam projection 242. Once the first cam follower 238 has passed the end of the cam spring 248, the cam spring 248 moves downwardly so as to engage and guide the second cam follower 240 upwardly when the direction of travel of the disk drive pusher 48 is reversed and pulled outward towards the extended position. In particular, when the disk drive pusher 48 is subsequently pulled outward towards the extended position, the cam spring 248 guides the second cam follower 240 upwardly so that the first cam follower 238 enters the upper pathway 244 and the knife blade 36 is retracted.

As explained above, the disk drive pusher 48 is pulled outwardly to initiate the testing procedure. During the outward motion of the disk drive pusher 48, the cam button 52 on the indexing disk drive arm 50 travels along one of the curvilinearly extending grooves 56 so as to rotate the indexing disk 30. During this outward motion, the first cam follower 238 on the knife blade assembly 58 travels along the upper pathway 244. As a result, the knife blade 36 is retracted from the knife slot 46 on the indexing disk 30 so that the indexing disk 30 is free to rotate in response to action of the cam button 52 in the curvilinearly extending groove 56. As the disk drive pusher 48 reaches the fully extended position, the first cam follower 238 passes the interior end 268 of the cam projection 242 and is guided into the lower pathway 246 by the biasing force of the spring 250 on the swing arm 230 of the knife blade assembly 58.

Prior to operating the sensor dispensing instrument 10, a sensor pack 300 must first be loaded into the sensor dispensing instrument 10 if one has not already been so loaded, or if all of the sensors 302 in the previously loaded sensor pack 300 have been used. To load a sensor pack 300, the lower case 24 and the upper case 18 are opened by depressing the latch 72 on the lower case 24. In the preferred embodiment shown, the opening of the lower case 24 and the upper case 18 causes the elastomeric connector 174 to separate from the contacts 166 on the autocal disk 158, thereby breaking the electrical connection between the autocal disk 158 and the electronics assembly 62. This causes an electronic counter (which is part of the electronics assembly 62) that keeps count of the number of unused sensors 302 in the sensor pack 300 to re-set to zero (0).

The opened housing 12 is then turned so that the lower surface 214 of the indexing disk 30 faces upwardly as shown in FIG. 3. A sensor pack 300 is then placed on the indexing disk 30 by aligning the notches 324 along the periphery of the sensor pack 300 with the pins 44 on the indexing disk 30. The lower case 24 is then pivoted on to the upper case 18 so as to enclose the sensor pack 300 within the housing. Once the lower case 24 is secured to the upper case 18 by the latch 72, the sensor dispensing instrument 10 is ready for operation.

The following is a brief description of the operation of the sensor dispensing instrument 10. First, the puller handle 32 is manually pulled from a standby position (FIG. 1) adjacent the rear end 16 of the housing 12 to an extended position (FIG. 6) away from the rear end 16 of the housing 12. The outward movement of the puller handle 32 causes the sensor dispensing instrument 10 to turn ON. The outward movement of the puller handle 32 also causes the cam button 52 on the indexing disk drive arm 50 to travel along one of the curvilinearly extending grooves 56 on the upper surface 216 of the indexing disk 30 so as to rotate the indexing disk 30 $\frac{1}{10}^{th}$ of a complete rotation. The rotation of the indexing disk 30 causes the sensor pack 300 to be rotated so that the next one of the sensor cavities 304 is placed in a standby position aligned with the testing end 14 of the housing 12. At the same time, the knife blade assembly 58 is retracted and moved towards the center of the indexing disk 30.

Next, the puller handle 32 is manually pushed inwardly from the extended position (FIG. 6) back past the standby position (FIG. 1) and into a testing position (FIG. 7). The inward movement of the puller handle 32 causes the knife blade assembly 58 to pivot downwardly so that a knife blade 36 pierces a portion of the protective foil 310 covering the sensor cavity 304 in the standby position and engages the sensor 302 in the sensor cavity 304. As the puller handle 32 continues to move back towards the housing 12, the knife blade assembly 58 forces the sensor 302 out of the sensor cavity 304 and into a testing position at the front end 14 of the housing 12. At the same time, the cam button 52 on the indexing disk drive arm 50 travels along one of the radially extending grooves 60 to prevent the indexing disk 30 from rotating.

After the sensor 302 has been completely ejected from the sensor cavity 304 and pushed into a testing position projecting out from the front end 14 of the housing 12, the sensor actuator 40 engages the sensor 302 to hold the sensor 302 in the testing position and to couple the sensor 302 to the electronics assembly 62. The front end 306 of the sensor is then inserted into a drop of blood to be tested, whereby the blood is analyzed by the electronics assembly 62. The results of the analysis are then displayed on the liquid crystal display 64 of the sensor dispensing instrument 10.

Once the analysis of the blood is complete, the button release 66 on the upper case 18 is depressed so as to disengage the sensor actuator 40 and release the sensor 302, which can be disposed of by tipping the front end 14 of the housing 12 downwardly.

While the invention has been described with reference to details of the illustrated embodiment, these details are not intended to limit the scope of the invention as defined in the appended claims. For example, the sensor dispensing instrument 10 can be used for testing fluids other than blood glucose. In fact, the sensor dispensing instrument 10 can be used in connection with the analysis of any type of chemistry fluid that can be analyzed by means of a reagent material.

The invention claimed is:

1. A sensor dispensing instrument adapted to handle a sensor pack containing a plurality of sensors, each of said plurality of sensors being disposed in a sensor cavity on said sensor pack and enclosed by a protective foil covering, said sensor dispensing instrument further adapted to perform a test using one of said plurality of sensors, said sensor dispensing instrument comprising:
an outer housing having a front end and a rear end, said outer housing further comprising a sensor slot through which one of said sensors is disposed to conduct the test;
a mechanism generally disposed within the outer housing, said mechanism including an indexing disk for supporting and rotating said sensor pack, an indexing support for rotating said indexing disk, an ejecting mechanism to eject one of said sensors from said sensor cavity and through said sensor slot, and a puller handle for moving said indexing support and the ejecting mechanism;
an electronics assembly generally disposed in the outer housing, said electronic assembly adapted to perform the test and display test results;
a sensor actuator generally disposed adjacent to the sensor slot, said sensor actuator adapted to engage with a sensor disposed in said sensor slot, to connect to contacts on the sensor, and to transmit electrical signals between the sensor and said electronics assembly; and
a sensor release generally disposed on a surface of the outer housing, said sensor release being moveable to disengage said sensor actuator from the sensor disposed in the sensor slot, said sensor release being adapted to move said puller handle and being adapted to disengage the sensor actuator such that the sensor can be removed from the instrument,
wherein the puller handle, the sensor release and sensor actuator are distinct and separate components.

2. The sensor dispensing instrument according to claim 1, wherein said puller handle is moveable between a testing position adjacent to the rear end of the outer housing and an extended position spaced outwardly from the rear end of the outer housing, and wherein said puller handle is moved from the testing position to the extended position to rotate said indexing disk, and is moved from the extended position to the testing position to puncture the covering and eject one of said sensors from said sensor cavity and through said sensor slot.

3. The sensor dispensing instrument according to claim 2, wherein the puller handle is moveable to a stand-by position, said stand-by position being located between the testing position and the extended position, wherein the sensor release is moved so as to move the puller handle from the testing position to the stand-by position and release the sensor from the sensor slot.

4. The sensor dispensing instrument according to claim 1, wherein the mechanical mechanism further comprises a movable disk drive pusher, said indexing support and said ejecting mechanism being mounted on said disk drive pusher, and said puller handle being affixed to a rear end of said disk drive pusher.

5. The sensor dispensing instrument according to claim 4, wherein the sensor actuator is engaged by a front end of said disk drive pusher to cause the sensor actuator to engage the sensor disposed in the sensor slot, and further wherein the sensor release engages the front end of the disk drive pusher to cause the sensor actuator to disengage from the sensor disposed in the sensor slot.

6. The sensor dispensing instrument according to claim 5, wherein the sensor release is moveable in a direction perpendicular to the movement of the disk drive pusher, and said sensor release comprises a sloped surface configure to engage the front end of the disk drive pusher at an angle so that the movement of the sensor release causes the disk drive pusher to move.

7. The sensor dispensing instrument according to claim 1, wherein the sensor release comprises a button that projects outwardly from the surface of the outer housing, said button being depressed to disengage the sensor actuator from the sensor disposed in the sensor slot.

8. The sensor dispensing instrument according to claim 1, wherein said electronics assembly comprises a printed circuit board electrically connected to said sensor actuator, electrical components mounted on the printed circuit board for conducting electronic functions in response to electrical signals, at least one button mounted on the printed circuit board for supplying electrical signals to the electrical components, and a liquid crystal display mounted on the printed circuit board for displaying said test results.

9. The sensor dispensing instrument according to claim 8, wherein the electronics assembly further comprises a communication interface mounted on the printed circuit board for connecting the sensor dispensing instrument to a separate electronic device.

10. The sensor dispensing instrument according to claim 8, wherein the electronics assembly further comprises battery terminals mounted on the printed circuit board for connecting to a battery, said battery for supplying electrical power to said electrical components.

11. A sensor dispensing instrument adapted to perform a test by using a fluid testing sensor, said fluid testing sensor being supplied by a disposable sensor pack inserted into said sensor dispensing instrument, said sensor pack having a plurality of sensor cavities covered by a protective covering, said fluid testing sensor being enclosed in one of said sensor cavities prior to the performance of said test, said sensor dispensing instrument comprising:

an outer housing having a front end and a rear end, said outer housing further comprising an upper case and a lower case, said upper case and said lower case being pivotally connected together near the rear end of the outer housing in a clam-like fashion to permit the outer housing to be opened to permit the insertion of the sensor pack;

a latch disposed near the front end of the outer housing and adapted to connect the upper case to the lower case so as to close said outer housing after the insertion of said sensor pack;

a sensor slot disposed at the front end of the outer housing, said sensor slot being adapted to receive said fluid testing sensor, said fluid testing sensor projecting outwardly through said sensor slot during the performance of said test;

an indexing disk for supporting and rotating said sensor pack, said indexing disk being rotatably mounted within said outer housing and comprising a plurality of curvilinearly extending grooves and a plurality of radially extending grooves, each radially extending groove being disposed between an adjacent pair of curvilinearly extending grooves;

a disk drive pusher generally disposed within said outer housing for rotating the indexing disk and ejecting the fluid testing sensor from said sensor pack, said disk drive pusher being laterally movable and comprising an indexing disk drive arm for rotating said indexing disk, said indexing disk drive arm being adapted to engage one of the curvilinearly extending grooves and the radially extending grooves, said disk drive pusher further comprising a knife blade assembly for ejecting the fluid testing sensor from the sensor pack, said knife blade assembly having a knife blade adapted to puncture said protective covering and engage the fluid testing sensor so as to eject said fluid testing sensor from said sensor cavity and through said sensor slot;

a puller handle generally disposed at the rear end the outer housing for moving said dish drive pusher, said puller handle being affixed to a rear end of the disk drive pusher, said puller handle being moveable between a testing position adjacent to the rear end of the outer housing and an extended position spaced outwardly from the rear end of the outer housing, wherein said puller handle is moved from the testing position to the extended position to rotate said indexing disk, and wherein said puller handle is moved from the extended position to the testing position to puncture the foil covering and eject said fluid testing sensor from said sensor cavity and through said sensor slot;

an electronics assembly for performing the test and displaying test results, said electronics assembly comprising a circuit board, electrical components mounted on the circuit board for conducting electronic functions in response to electrical signals, a plurality of buttons mounted on the circuit board for supplying electrical signals to the electrical components, a liquid crystal display mounted on the printed circuit board for displaying said test results;

a sensor actuator disposed within said outer housing adjacent to said sensor slot for connecting the fluid testing sensor to the electronics assembly, said sensor actuator adapted to engage and hold said fluid testing sensor in said sensor slot when said puller handle is in the testing position, said sensor actuator having metal contacts adapted to connect to contacts on the fluid testing sensor when said fluid sensor testing sensor is disposed in said sensor slot and when said puller handle is in the testing position so as to transmit electrical signals between said fluid testing sensor and the printed circuit board of said electronics assembly; and a sensor release generally disposed on a surface of the outer housing, said sensor release being movable to disengage said sensor actuator from the fluid testing sensor disposed in the sensor slot and permit said fluid testing sensor to be discharged from said sensor slot and removed from the instrument, said sensor being adapted to move the puller handle from the testing components, wherein the puller handle, the sensor release and sensor actuator are distinct and separate components.

12. The sensor dispensing instrument according to claim 11, wherein the puller handle is moveable to a stand-by position, said stand-by position being located between the testing position and the extended position, wherein the metal contacts of said sensor actuator are disconnected from the contacts on said fluid testing sensor when said puller handle is moved from the testing position to the stand-by position, and further wherein said puller handle is moved from said testing position to said stand-by position by the movement of the sensor release.

13. The sensor dispensing instrument according to claim 11, wherein the sensor actuator is engaged by a front end of said disk drive pusher to cause the sensor actuator to engage the fluid testing sensor disposed in the sensor slot, and further wherein the sensor release engages the front end of the disk drive pusher to cause the sensor actuator to disengage from the fluid testing sensor disposed in the sensor slot.

14. The sensor dispensing instrument according to claim 13, wherein the sensor release is moveable in a direction perpendicular to the movement of the disk drive pusher, and said sensor release comprises a sloped surface configure to engage the front end of the disk drive pusher at an angle so that the movement of the sensor release causes the disk drive pusher to move.

15. The sensor dispensing instrument according to claim 11, wherein the sensor release comprises a button that projects outwardly from the surface of the outer housing, said button being depressed to disengage the sensor actuator from the fluid testing sensor disposed in the sensor slot.

16. A method of operating a sensor dispensing instrument adapted to handle a sensor pack containing a plurality of sensors, each of said plurality of sensors being disposed in a sensor cavity on said sensor pack and enclosed by a protective covering, and said sensor dispensing instrument further adapted to perform a test using one of said plurality of sensors, said sensor dispensing instrument comprising an outer housing having a sensor slot disposed therein through which one of said sensors is disposed to conduct the test, said sensor dispensing instrument further comprising a mechanism having an indexing disk for supporting and rotating said sensor pack, an indexing support for rotating said indexing disk, an ejecting mechanism to eject one of said sensors from said sensor cavity and through said sensor slot, a puller handle and a sensor release, said puller handle being moveable between a testing position adjacent to a rear end of the outer housing, an extended position spaced outwardly from the rear end of the outer housing, and a stand-by position located between the testing position and the extended position, said method comprises the acts of:

a) grasping said puller handle when said puller handle is in the stand-by position;

b) pulling said puller handle from the stand-by position to the extended position so as to move said indexing support;

c) pushing said puller handle from the extended position to the testing position so as to move said disk indexing support and cause said ejecting mechanism to eject one of said sensors from said sensor cavity and through said sensor slot;

d) performing the test by using the sensor disposed in said sensor slot; and e) activating said sensor release to engage said indexing support and move the puller handle from the testing position to the stand-by position so as to cause the sensor to be released from the sensor slot, the puller handle and the sensor release being distinct and separate components.

17. The method of claim 16, wherein the sensor dispensing instrument further comprises a sensor actuator generally disposed adjacent to the sensor slot and adapted to engage with a sensor disposed in said sensor slot when said puller handle is in the testing position, and act (c) includes engaging said sensor actuator with the sensor disposed in said sensor slot, and includes disengaging said sensor actuator from said sensor disposed in said sensor slot.

18. The method of claim 16, wherein the sensor release comprises a button, and the act of activating the sensor release in act (e) comprises depressing said button.

19. The sensor dispensing instrument according to claim 1, wherein the protective covering is foil.

20. The sensor dispensing instrument according to claim 11, wherein the protective covering is foil.

21. The method of claim 16, wherein the protective covering is foil.

22. The method of claim 16, wherein the sensor release comprises a button that projects outwardly from the surface of the outer housing, said button being depressed to disengage the sensor actuator from the sensor disposed in the sensor slot.

23. The method of claim 16, wherein the grasping of said puller handle is between a finger and a thumb of a user hand.

24. The sensor dispensing instrument according to claim 1, wherein the sensor release comprises a button that projects outwardly from the surface of the outer housing, said button being adapted to be depressed so as to disengage the sensor actuator from the sensor disposed in the sensor slot.

25. The sensor dispensing instrument according to claim 2, wherein the sensor release comprises a button that has a sloped contact surface that engages a front end of the puller handle, the sloped contact surface configured to slide along the front end of the puller handle thereby moving the puller handle from the testing position into a standby position so as to disengage the sensor actuator from the sensor disposed in the sensor slot.

26. The sensor dispensing instrument according to claim 25, wherein the standby position is between the testing position and the extended position.

27. The sensor dispensing instrument according to claim 25, wherein the button is configured to be depressed in a direction perpendicular to the direction of movement of the puller handle.

* * * * *

UNITED STATES PATENT AND TRADEMARK OFFICE
CERTIFICATE OF CORRECTION

PATENT NO. : 7,611,899 B2
APPLICATION NO. : 10/206345
DATED : November 3, 2009
INVENTOR(S) : Robert C. Whitson et al.

It is certified that error appears in the above-identified patent and that said Letters Patent is hereby corrected as shown below:

In Claim 1, Column 17, Line 48, change "sensor pack and enclosed by a protective foil covering, said" to "sensor pack and enclosed by a protective covering, said"

In Claim 4, Column 18, Lines 29-30, change "wherein the mechanical mechanism further comprises a movable" to "wherein the mechanism further comprises a moveable"

In Claim 11, Column 19, Line 40, change "pusher being laterally movable and comprising an" to "pusher being laterally moveable and comprising an"

In Claim 11, Column 19, Lines 51-52, change "a puller handle generally disposed at the rear end the outer housing for moving said dish drive pusher, said puller" to "a puller handle generally disposed at the rear end of the outer housing for moving said disk drive pusher, said puller"

In Claim 11, Column 19, Line 61-62, change "position to the testing position to puncture the foil covering" to "position to the testing position to puncture the protective covering"

In Claim 11, Column 20, Line 4-5, change "display mounted on the printed circuit board for displaying" to "display mounted on the circuit board for displaying"

In Claim 11, Column 20, Line 16, change "fluid testing sensor and the printed circuit board of said" to "fluid testing sensor and the circuit board of said"

In Claim 11, Column 20, Line 19, change "housing, said sensor release being movable to disengage" to "housing, said sensor release being moveable to disengage"

In Claim 11, Column 20, Line 23, change "removed from the instrument, said sensor being adapted" to "removed from the instrument, said sensor release being adapted"

In Claim 11, Column 20, Line 24, change "to move the puller handle from the testing components," to "to move the puller handle from the testing position,"

In Claim 16, Column 21, Line 16, change "the testing position so as to move said disk indexing" to "the testing position so as to move said indexing"

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,611,899 B2 Page 1 of 1
APPLICATION NO. : 10/206345
DATED : November 3, 2009
INVENTOR(S) : Whitson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 814 days.

Signed and Sealed this

Twelfth Day of October, 2010

David J. Kappos
*Director of the United States Patent and Trademark Office*